(12) United States Patent
Fritzinger et al.

(10) Patent No.: US 8,728,082 B2
(45) Date of Patent: May 20, 2014

(54) BONE PLATE POSITIONING SCAFFOLD

(75) Inventors: Daniel Duane Fritzinger, Warsaw, IN (US); Donald Lee, Nashville, TN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 329 days.

(21) Appl. No.: 13/116,257

(22) Filed: May 26, 2011

(65) Prior Publication Data

US 2012/0303068 A1 Nov. 29, 2012

(51) Int. Cl.
*A61B 17/80* (2006.01)
*A61B 17/56* (2006.01)

(52) U.S. Cl.
USPC .......................... 606/86 B; 606/286; 606/96

(58) Field of Classification Search
USPC ............... 606/70, 71, 86 B, 96–98, 280–299; 269/82–85
See application file for complete search history.

(56) References Cited

U.S. PATENT DOCUMENTS

| 2,583,896 | A | | 1/1952 | Siebrandt |
| 8,486,114 | B2 * | | 7/2013 | Gillard et al. ................. 606/280 |
| 2003/0100902 | A1 * | 5/2003 | Wellisz et al. ................. 606/72 |
| 2005/0283155 | A1 * | 12/2005 | Jacene et al. .................. 606/70 |
| 2010/0292696 | A1 * | 11/2010 | Chantelot et al. ............. 606/70 |
| 2011/0106183 | A1 | 5/2011 | Deel'oca |

FOREIGN PATENT DOCUMENTS

DE  10 2009 042701 A1  3/2011
WO  WO 99/45856 A1  9/1999

* cited by examiner

*Primary Examiner* — Christopher Beccia
(74) *Attorney, Agent, or Firm* — Ryan O. White; Taft Stettinius & Hollister LLP

(57) ABSTRACT

A device to maintaining temporary engagement with a bone plate and a bone, the device comprising: (a) a first biased appendage positioned opposite a second biased appendage, the first and second biased appendages including an arcuate vertical profile that partially defines an interior region; (b) a platform concurrently coupled to the first and second biased appendages, the platform also partially defining the interior region, the platform including a through hole open to the interior region; and, (c) a first tab extending from at least one of the first biased appendage, the second biased appendage, and the platform, the first tab extending into the interior region to engage a bone plate.

19 Claims, 17 Drawing Sheets

BONE PLATE POSITIONING SCAFFOLD

RELATED ART

1. Field of the Invention

The present disclosure is directed to devices used to initially position and retain a bone plate with respect to a bone and, more specifically, includes a clip-on device for use with a volar bone plate to retain the bone plate in position with respect to a radius.

2. Brief Discussion of Related Art

In the context of distal radius fractures, a bone plate (known as a volar plate) is commonly mounted to the radius (also include radius bone segments resulting from the fracture) in order to ensure the radius is in a proper orientation to promote bone growth at the fracture site(s). It is often desirable for a surgeon when mounting the volar plate to the radius to temporarily hold the volar plate in the appropriate position before retention screws are concurrently mounted to the volar plate and the radius or radius segments.

In the past, ratcheting forceps were utilized to concurrently scaffold the volar plate and the radius. One of the primary problems with ratcheting forceps is that the forceps tend to be bulky and obstruct an unnecessary amount of the surgeon's working area. Moreover, ratcheting forceps are sometimes difficult to apply and loosen during the surgical procedure.

Accordingly, there is a need for an alternative to ratcheting forceps that may be used to temporarily secure a bone plate to a bone.

INTRODUCTION TO THE INVENTION

The present disclosure is directed to devices used to initially position and retain a bone plate with respect to a bone. More specifically, the disclosure includes embodiments characterized as clip-on devices that partially circumscribe a bone in order to temporarily retain the position of a bone plate with respect to a bone. While the exemplary embodiment is explained with respect to a volar plate, it should be understood that the exemplary embodiment may be used to temporarily retain the position of a bone plate with respect to any number of bones. Thus, the disclosure is by no means limited to radius fractures and volar plates.

It is a first aspect of the present invention to provide a device to maintain temporary engagement with a bone plate and a bone, the device comprising: (a) a first biased appendage positioned opposite a second biased appendage, the first and second biased appendages including an arcuate vertical profile that partially defines an interior region; (b) a platform concurrently coupled to the first and second biased appendages, the platform also partially defining the interior region, the platform including a through hole open to the interior region; and, (c) a first tab extending from at least one of the first biased appendage, the second biased appendage, and the platform, the first tab extending into the interior region and adapted to engage a bone plate.

In a more detailed embodiment of the first aspect, the device further includes a third biased appendage positioned opposite a fourth biased appendage, the third and fourth biased appendages including an arcuate vertical profile that partially defines the interior region, wherein the first and third biased appendages are spaced apart in a proximal-to-distal direction, and wherein the first and second biased appendages are spaced apart in a medial-to-lateral direction perpendicular to the proximal-to-distal direction. In yet another more detailed embodiment, at least one of the first and second biased appendages and the platform includes a K-wire hole. In a further detailed embodiment, at least one of the first and second biased appendages and the platform include a plurality of K-wire holes. In still a further detailed embodiment, the platform includes an arcuate medial-to-lateral profile, and the first and second biased appendages seamlessly extend from the platform. In a more detailed embodiment, the platform includes at least one K-wire hole extending into the interior region, and the through hole of the platform comprises an oblong through hole sized to receive a threaded fastener. In a more detailed embodiment, the first tab extends from a bottom surface of the platform, the bottom surface of the platform includes a second tab spaced apart from the first tap in a medial-to-lateral direction, the first biased appendage is spaced apart from the second biased appendage in the medial-to-lateral direction, and the first and second tabs cooperate to decrease a widthwise gap in the interior region extending in the medial-to-lateral direction. In another more detailed embodiment, the device further includes a second tab extending from at least one of the first biased appendage, the second biased appendage, and the platform, the second tab extending into the interior region and adapted to engage the bone plate, where the second tab is spaced apart from the first tap in the medial-to-lateral direction, and the first and second tabs cooperate to decrease a first widthwise gap in the interior region extending in the medial-to-lateral direction. In yet another more detailed embodiment, the device further includes a second tab extending from at least one of the first biased appendage, the second biased appendage, and the platform, the second tab extending into the interior region and adapted to engage the bone plate, a third tab extending from at least one of the first biased appendage, the second biased appendage, and the platform, the third tab extending into the interior region and adapted to engage the bone plate, and a fourth tab extending from at least one of the first biased appendage, the second biased appendage, and the platform, the fourth tab extending into the interior region and adapted to engage a bone plate, where the second tab is spaced apart from the first tab in the medial-to-lateral direction and cooperate to decrease a first widthwise gap in the interior region extending in the medial-to-lateral direction, where the fourth tab is spaced apart from the third tab in the medial-to-lateral direction and cooperate to decrease a second widthwise gap in the interior region extending in the medial-to-lateral direction and where the first tab is spaced apart from the third tab in the proximal-to-distal direction.

In yet another more detailed embodiment of the first aspect, the first tab extends from the first biased appendage, a second tab extends from the second biased appendage, a third tab extends from the third biased appendage, and a fourth tab extends from the fourth biased appendage. In still another more detailed embodiment, the device further includes a drill guide block operatively coupled to at least one of the first biased appendage, the second biased appendage, and the platform, the drill guide block including at least one through orifice. In a further detailed embodiment, the drill guide block includes a through orifice partially defined by a plurality of arcuate walls. In still a further detailed embodiment, the drill guide block is integrally formed with at least one of the first biased appendage, the second biased appendage, and the platform. In a more detailed embodiment, the first biased appendage, the second biased appendage, and the platform are integrally formed, and the drill guide block is integrally formed with the first biased appendage, the second biased appendage, and the platform. In a more detailed embodiment, the drill guide block is shaped to conform to a volar bone plate. In another more detailed embodiment, the through hole of the platform comprises an oblong through hole adapted to receive a threaded fastener, and at least a portion of the oblong through hole is delineated by an oblong ring upstanding from a top surface of the platform. In yet another more detailed embodiment, the device further includes a first arcuate flange mounted to a distal portion of the platform, and a second arcuate flange mounted to a proximal portion of the platform.

In yet another more detailed embodiment of the first aspect, at least one of the first and second biased appendages comprises a first closed loop. In still another more detailed embodiment, the device further includes a first biased detent extending from at least one of the first biased appendage, the second biased appendage, and the platform, the first biased detent including a range of motion at least partially overlapping a through passage delineated by the first closed loop. In a further detailed embodiment, the first biased appendage includes a first closed loop, and the second biased appendage includes a second closed loop. In still a further detailed embodiment, the device further includes a first biased detent extending from at least one of the first biased appendage, the second biased appendage, and the platform, the first biased detent including a range of motion at least partially overlapping a through passage delineated by at least one of the first closed loop and the second closed loop. In a more detailed embodiment, the device further includes a first biased detent extending from the first biased appendage and including a range of motion at least partially overlapping a through passage delineated by the first closed loop, and a second biased detent extending from the second biased appendage and including a range of motion at least partially overlapping a through passage delineated by the second closed loop. In a more detailed embodiment, the first and second biased detents cooperate to decrease a widthwise gap in the interior region extending in a medial-to-lateral direction, and the first and second loops extend in a proximal-to-distal direction perpendicular to the medial-to-lateral direction. In another more detailed embodiment, the arcuate profile of the first biased appendage creates a concave side and an opposite convex side, the arcuate profile of the second biased appendage creates a concave side and an opposite convex side, and the concave side of the first biased appendage faces the concave side of the second biased appendage. In yet another more detailed embodiment, the arcuate profile of the first biased appendage creates a concave side and an opposite convex side, the arcuate profile of the second biased appendage creates a concave side and an opposite convex side, the arcuate profile of the third biased appendage creates a concave side and an opposite convex side, the arcuate profile of the fourth biased appendage creates a concave side and an opposite convex side, the concave side of the first biased appendage faces the concave side of the second biased appendage, and the concave side of the third biased appendage faces the concave side of the fourth biased appendage. In still a further detailed embodiment, at least one of the first biased appendage, the second biased appendage, and the platform includes a projection extending into the interior region, the projection spaced apart from the tab and having a longitudinal arcuate surface exposed to the interior region.

It is a second aspect of the present invention to provide a device to maintaining temporary engagement with a bone plate and a bone, the device comprising: (a) a first biased appendage having a vertical arcuate profile that bows outward in a medial direction; (b) a second biased appendage positioned opposite the first biased appendage, the second biased appendage having a vertical arcuate profile that bows outward in a lateral direction, opposite the medial direction; (c) a platform concurrently coupled to the first and second biased appendages, the platform cooperates with the first biased appendage and the second biased appendage to partially define an interior region, the platform including an oblong through hole open to the interior region, where at least one of the first biased appendage, the second biased appendage, and the platform includes a K-wire hole extending therethrough.

DETAILED DESCRIPTION

Figure 1:
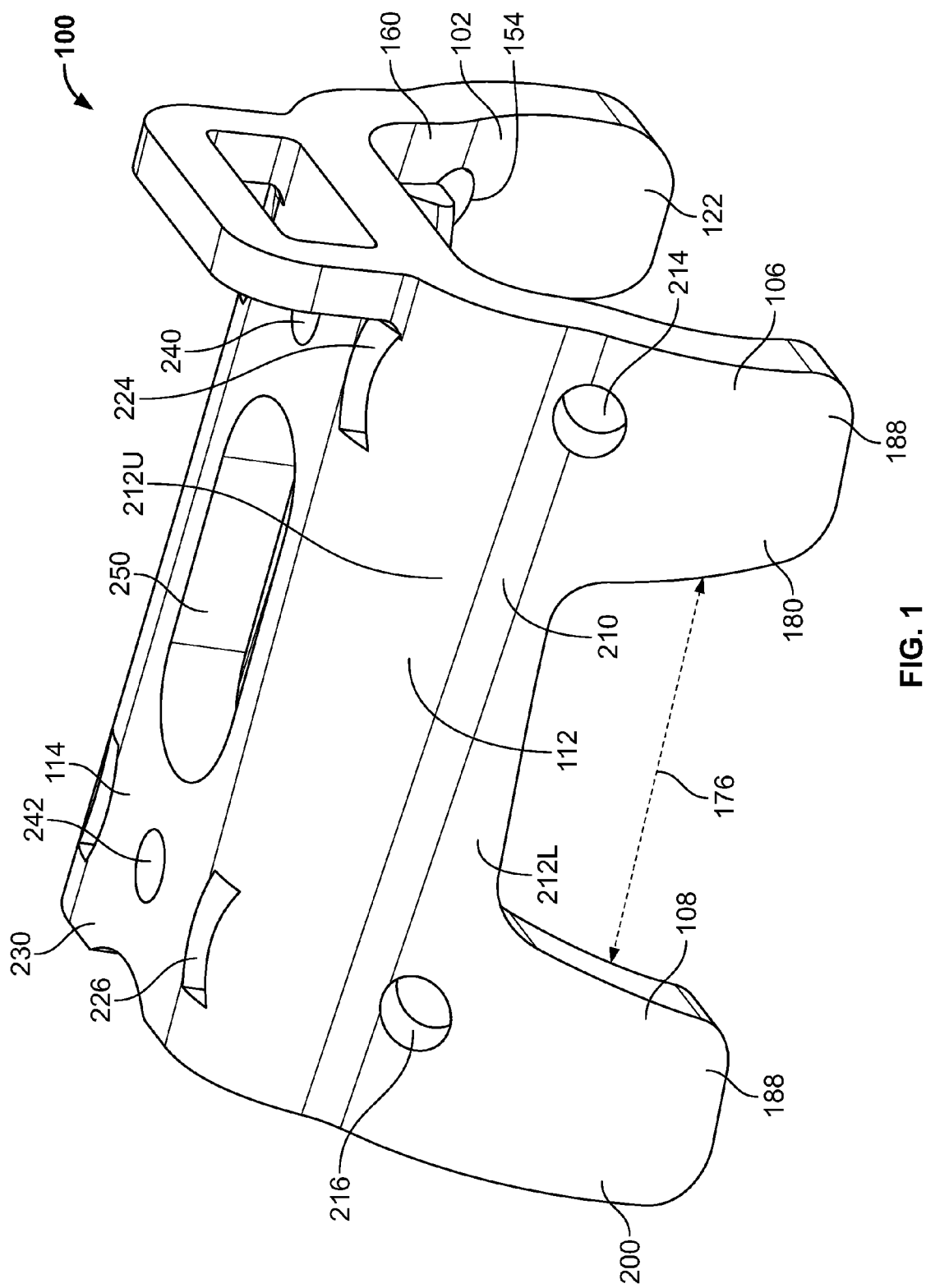
FIG. 1 is an elevated perspective view, from the front, of a first exemplary bone plate scaffold.
Figure 2:
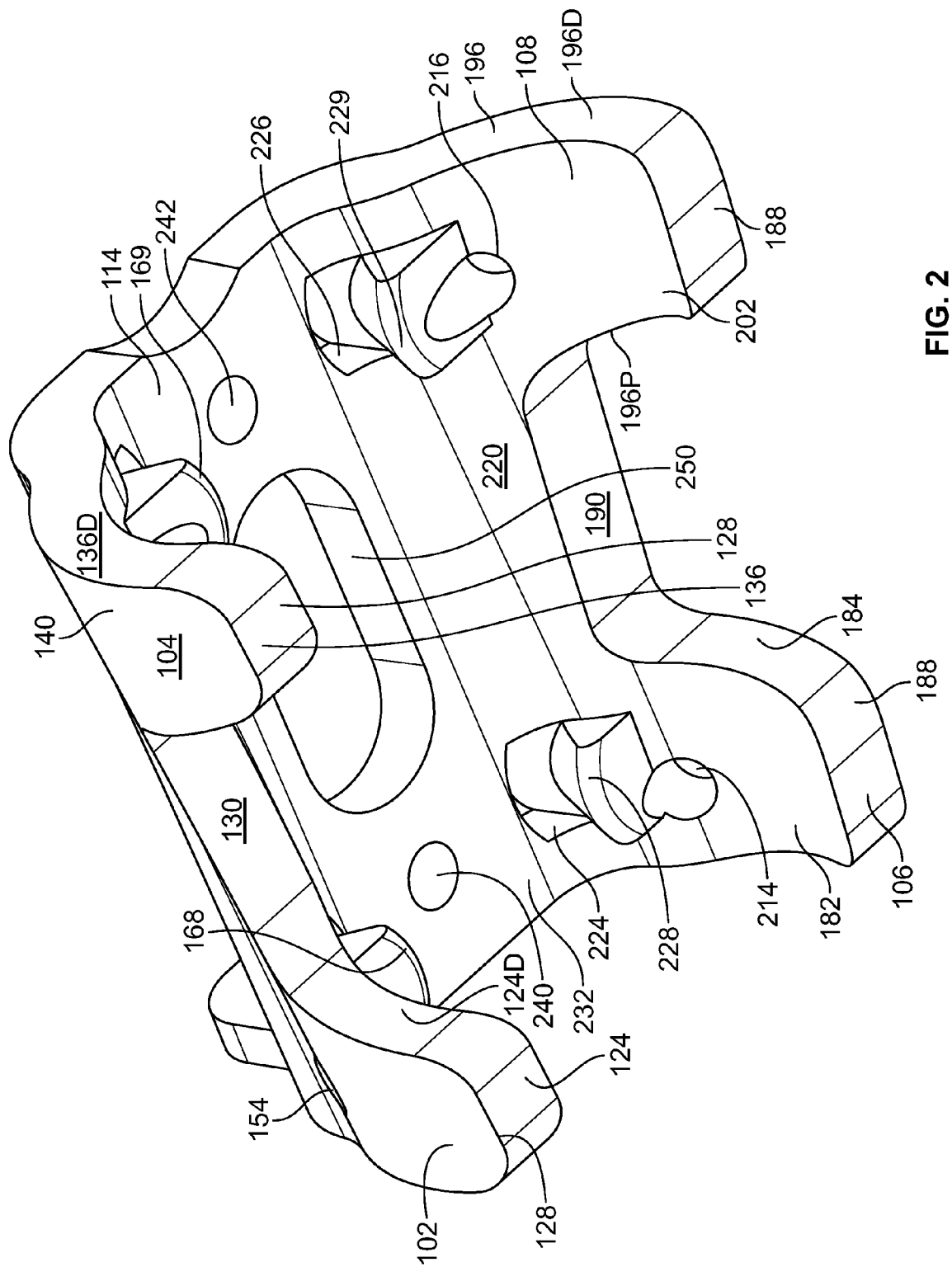
FIG. 2 is a bottom perspective view of the exemplary bone plate scaffold of FIG. 1.
Figure 3:
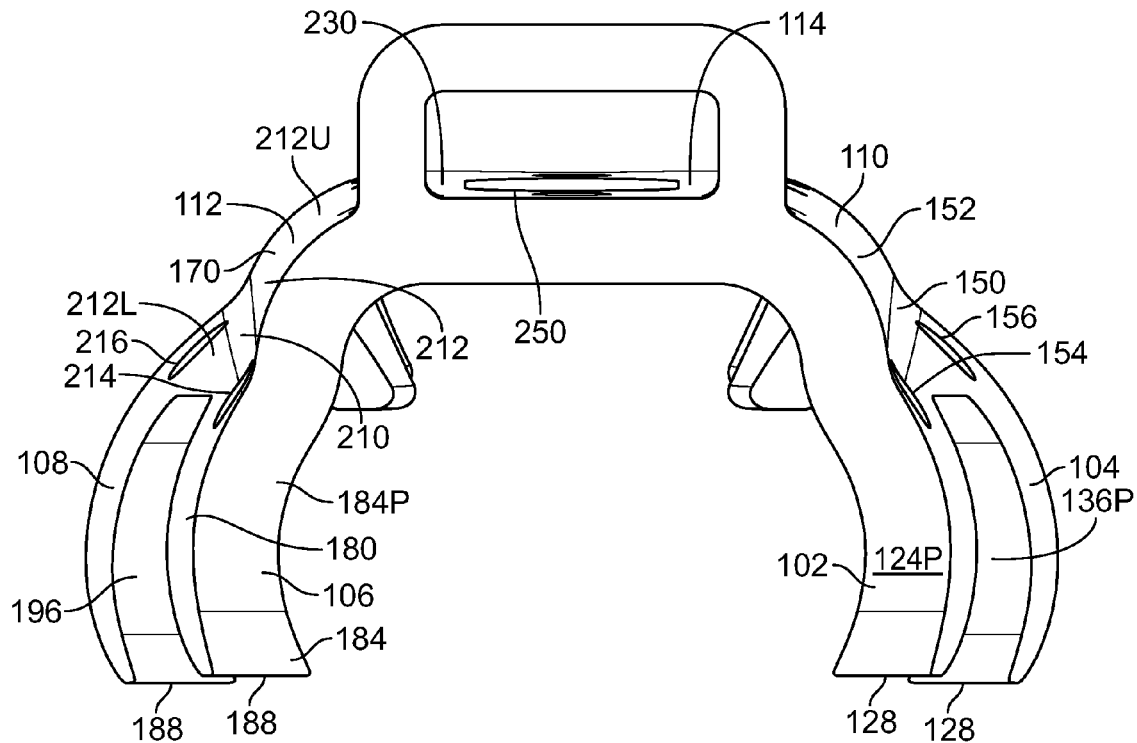
FIG. 3 is a rear view of the exemplary bone plate scaffold of FIG. 1.
Figure 4:
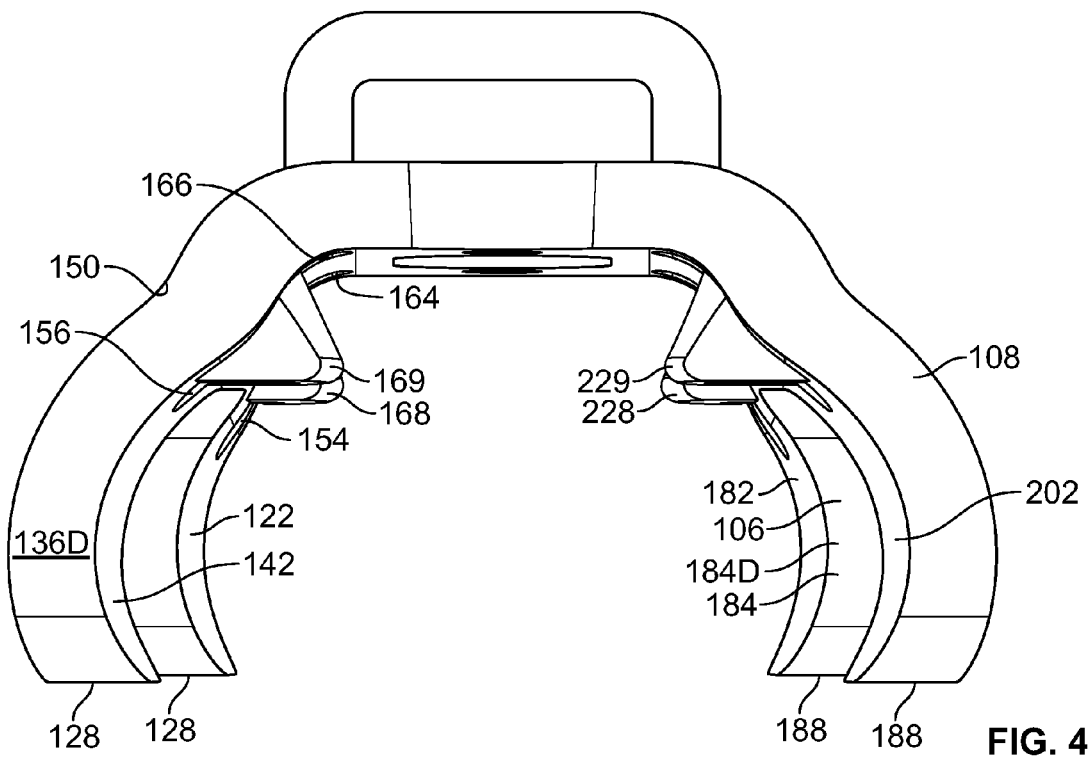
FIG. 4 is a frontal view of the exemplary bone plate scaffold of FIG. 1.
Figure 5:
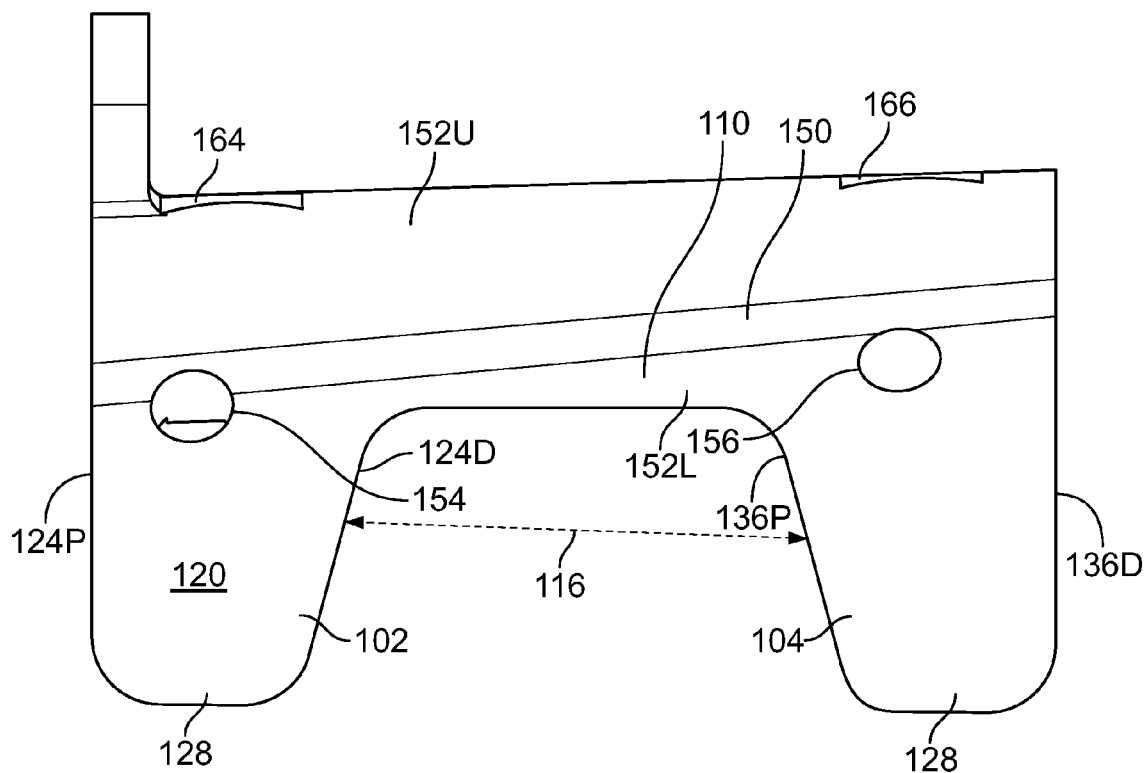
FIG. 5 is a left side, profile view of the exemplary bone plate scaffold of FIG. 1.

The exemplary embodiments of the present invention are described and illustrated below to encompass devices utilized to temporarily retain the position of a bone plate with respect to a bone and associated methods. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Referencing FIGS. 1-5, an exemplary scaffold 100 includes a generally arcuate shape to partially circumscribe a bone. This arcuate shape is partially defined by four arcuate arms 102, 104, 106, 108 (lateral proximal, lateral distal, medial proximal, medial distal) that seamlessly extend respectively from lateral and medial walls 110, 112. Interposing the lateral and medial walls 110, 112 is a base 114, which seamlessly transitions into the medial and lateral walls.

On one side of the scaffold 100, the lateral proximal arm 102 is longitudinally spaced apart from the lateral distal arm 104 by a predetermined space 116. The lateral proximal arm 102 includes an arcuate outer surface 120 and arcuate interior surface 122. A peripheral surface 124 bridges the outer and inner surfaces 120, 122. The outer surface 120 is convex, while the interior surface 122 is concave. In exemplary form, each arm 102, 104 includes a rounded end 128 that, moving arcuately toward the base 114, progressively becomes wider until reaching the lateral wall 110. The peripheral surface 124 on the proximal side 124P of the proximal arm 102 is substantially vertical, whereas the peripheral surface 124D on the distal side of the proximal arm is non-vertical and takes on an arcuate, convex shape in the proximal-to-distal direction. The peripheral surface 124D seamlessly transitions into a peripheral wall surface 130, which is part of the lateral wall 110.

The peripheral wall surface 130 of the lateral wall 110 seamlessly transitions into a peripheral surface 136 extending around the lateral distal arm 104. As with the lateral proximal arm 102, the lateral distal arm includes an arcuate outer surface 140 and arcuate interior surface 142. The outer surface 140 is convex, while the interior surface 142 is concave. The peripheral surface 136 on the distal side 136D of the distal arm 104 is substantially vertical, whereas the peripheral surface 136P on the proximal side of the distal arm is non-vertical and takes on an arcuate, convex shape in the distal-to-proximal direction until transitioning into the peripheral wall surface 130 of the lateral wall 110.

The lateral wall 110 takes on a gentle S-shaped profile when viewed from a vertical cross section. A longitudinal depression 150 is formed into an exterior surface 152 of the lateral wall. The longitudinal depression 150 operates to delineate a lower portion 152L of the surface that has the same arcuate profile as the lateral arms 102, 104 from an upper portion 152U of the surface having its own arcuate profile. Two orifices 154, 156 extend through the lower portion 152L of the exterior surface and also through an interior surface 160 of the lateral wall 110. The lateral proximal orifice 154 is positioned above the lateral proximal arm 102, whereas the lateral distal orifice 156 is positioned above the lateral distal arm 104. Each orifice 154, 156 is sized to accommodate a K-wire (not shown). Two other orifices 164, 166 extend through the upper portion 152U of the exterior surface and also through the interior surface 160 of the lateral wall 110. One orifice 164 is positioned above the lateral proximal orifice 154, whereas the other orifice 166 is positioned above the lateral distal orifice 156. Each orifice 164, 166 is sized to accommodate a K-wire (not shown) extending beyond the interior surface 160.

The interior surface 160 includes a pair of raised tabs 168, 169 that are located between corresponding orifices 154, 156, 164, 166. As will be discussed in more detail hereafter, the tabs 168, 169 cooperate with the other pair of raised tabs 228, 229 to temporarily retain a bone plate in relative position while fasteners are concurrently mounted to the bone and bone plate.

Opposite the lateral side of the scaffold 100, the medial proximal arm 106 is longitudinally spaced apart from the medial distal arm 108 by a predetermined space 176. The medial proximal arm 106 includes an arcuate outer surface 180 and arcuate interior surface 182. A peripheral surface 184 bridges the outer and inner surfaces 180, 182. The outer surface 180 is convex, while the interior surface 182 is concave. In exemplary form, each arm 106, 108 includes a rounded end 188 that, moving arcuately toward the base 114, progressively becomes wider until reaching the medial wall 170. The peripheral surface 184 on the proximal side 184P of the proximal arm 106 is substantially vertical, whereas the peripheral surface 184D on the distal side of the proximal arm is non-vertical and takes on an arcuate, convex shape in the proximal-to-distal direction. The peripheral surface 184D seamlessly transitions into a peripheral wall surface 190, which is part of the medial wall 170.

The peripheral wall surface 190 of the medial wall 170 seamlessly transitions into a peripheral surface 196 extending around the medial distal arm 108. As with the medial proximal arm 106, the medial distal arm includes an arcuate outer surface 200 and arcuate interior surface 202. The outer surface 200 is convex, while the interior surface 202 is concave. The peripheral surface 196 on the distal side 196D of the distal arm 108 is substantially vertical, whereas the peripheral surface 196P on the proximal side of the distal arm is non-vertical and takes on an arcuate, convex shape in the distal-to-proximal direction until transitioning into the peripheral wall surface 190 of the medial wall 170.

The medial wall 170 takes on a gentle S-shaped profile when viewed from a vertical cross section. A longitudinal depression 210 is formed into an exterior surface 212 of the medial wall. The longitudinal depression 210 operates to delineate a lower portion 212L of the surface that has the same arcuate profile as the medial arms 106, 108 from an upper portion 212U of the surface having its own arcuate profile. Two orifices 214, 216 extend through the lower portion 212L of the exterior surface and also through an interior surface 220 of the medial wall 170. The medial proximal orifice 214 is positioned above the medial proximal arm 106, whereas the medial distal orifice 216 is positioned above the medial distal arm 108. Each orifice 214, 216 is sized to accommodate a K-wire (not shown). Two other orifices 224, 226 extend through the upper portion 212U of the exterior surface and also through the interior surface 220 of the medial wall 170. One orifice 224 is positioned above the medial proximal orifice 214, whereas the other orifice 226 is positioned above the medial distal orifice 216. Each orifice 224, 226 is sized to accommodate a K-wire (not shown). The interior surface 220 includes a pair of raised tabs 228, 229 that are located between corresponding orifices 214, 216, 224, 226.

Interposing the medial and lateral sides of the scaffold 100 is the base 114. The base 114 comprises a top, planar surface 230 that is opposite a bottom, planar surface 232. Two orifices 240, 242 (proximal and distal) extend through the top surface 230 and through the bottom surface 232. Each orifice 240, 242 is sized to receive a respective K-wire (not shown). It should be noted that the proximal K-wire orifices 240, 154, 164, 214, 224 all lay along a first arcuate path, while the distal K-wire orifices 242, 156, 166, 216, 226 all lie along a second arcuate path. These arcuate paths are parallel to one another and are longitudinally spaced from one another. In between these arcuate paths, extending through the base is an elongated hole 250. This elongated hole 250 is sized to allow throughput of a variable angle locking screw or a compression screw (not shown) in order to interface one or more orifices associated with a bone plate.

Each of the raised tabs 169, 168 228, 229 includes an arcuate inclined surface 260 that rounds over to form a ledge 262 that is substantially parallel with the top planar surface 230. As will be discussed in more detail hereafter, the ledge 262 is adapted to rest against the top surface of the bone so that the bone is sandwiched by the ledge and the interior surface 122, 142, 182, 202 proximate the rounded ends 128, 188 of the arcuate arms 102, 104, 106, 108.

In this exemplary embodiment, the scaffold 100 described above is fabricated from injection molded thermoplastic. As a result, the components and features of the scaffold 100 described above are integrated into a single piece structure thus giving the material some inherent elasticity and flexibility. But it should also be noted that the scaffold 100 need not be fabricated from a thermoplastic material or injection molded. Instead, the scaffold 100 may be fabricated from a metal such as, without limitation, aluminum.

It should also be understood that the dimensions of the scaffold as described herein are exemplary in nature and may be changed to accommodate various sizes and shapes of bones and bone plates. For example, the scaffold 100 may be enlarged for use as a femoral fracture device.

The first exemplary scaffold 100 may include a block (not shown) that may be a separate component or may be integrally formed as part of the scaffold. The block operates to aid surgeons in aligning threaded drill guides (not shown) with holes extending through the bone plate. In exemplary form, the block includes an outline that tracks the shape of a portion of a volar bone plate (see FIG. 6). More specifically, the block includes a series of angled through orifices that at least partially overlap with one another. The walls that partially define the through orifices are correspondingly angled so that when the drill guide (not shown) is aligned with a respective through hole of the bone plate, the drill guide can only be axially inserted in a single angle. In this manner, the drilled hole in the bone is assured to be axially aligned with the respective through hole. Those skilled in the art are familiar with drill guides and understand the principle of the block without further explanation.

The block includes a pair of proximal projections that overhang from the remainder of the block. These projections are received within respective distal through holes 166, 226 of the scaffold 100 to form a snap-fit between the block and scaffold. In this manner, the block is mounted to the scaffold 100 after the bone plate is in position with respect to the bone.

Figure 6:
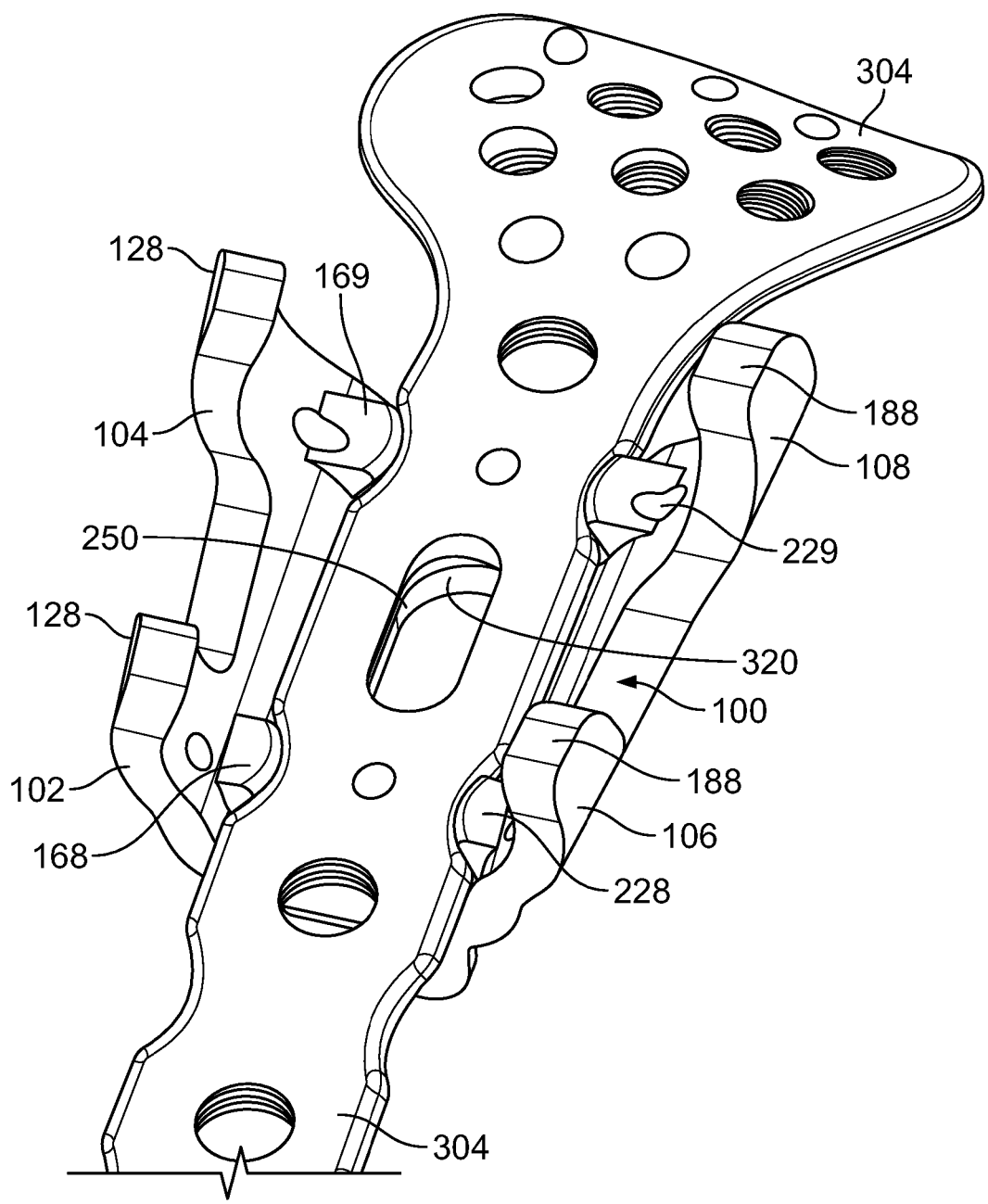
FIG. 6 is a bottom view of the exemplary bone plate scaffold of FIG. 1 coupled to a bone plate.
Figure 7:
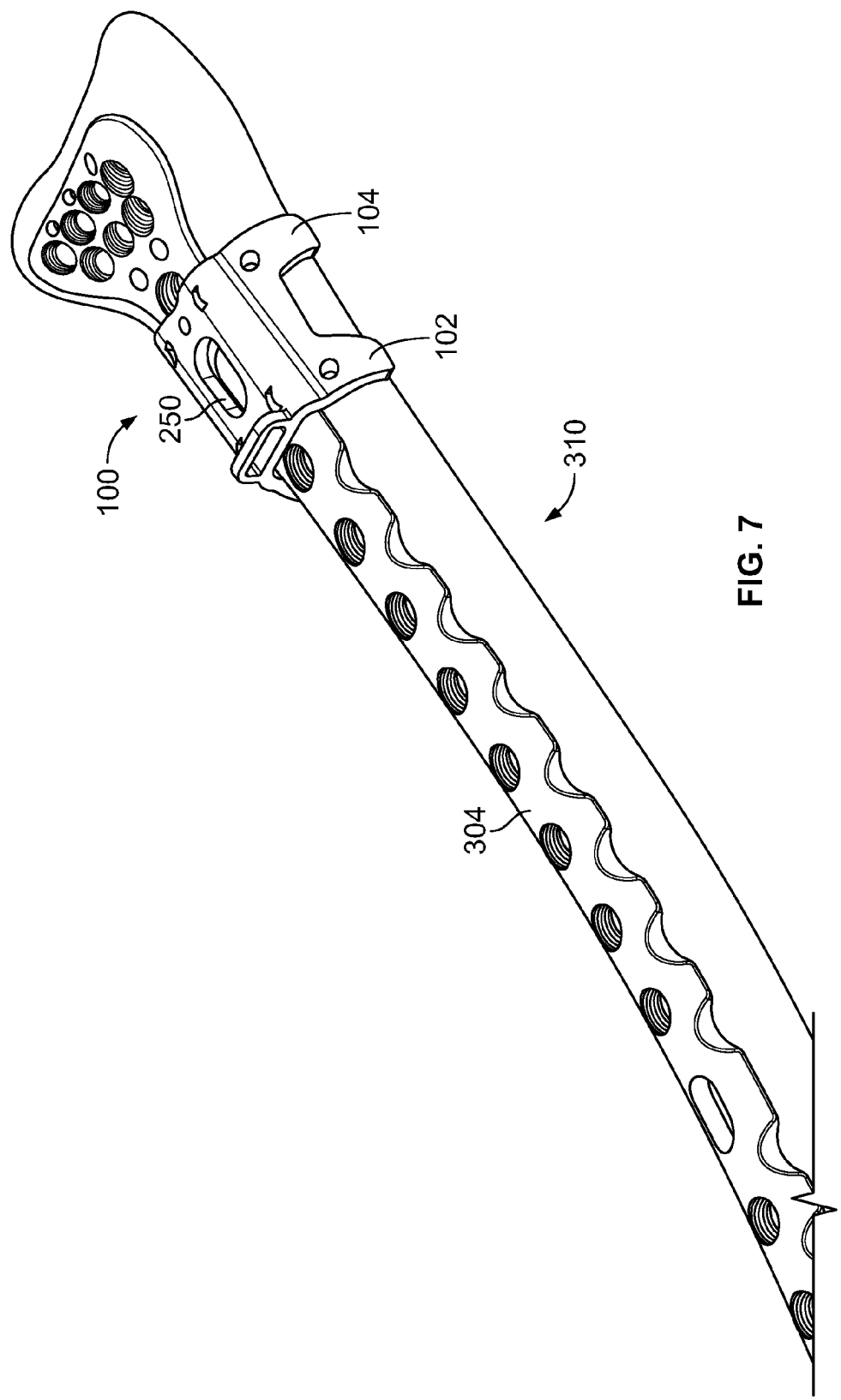
FIG. 7 is an elevated perspective view of the exemplary bone plate scaffold of FIG. 1 coupled to a bone plate and a bone.
Figure 8:
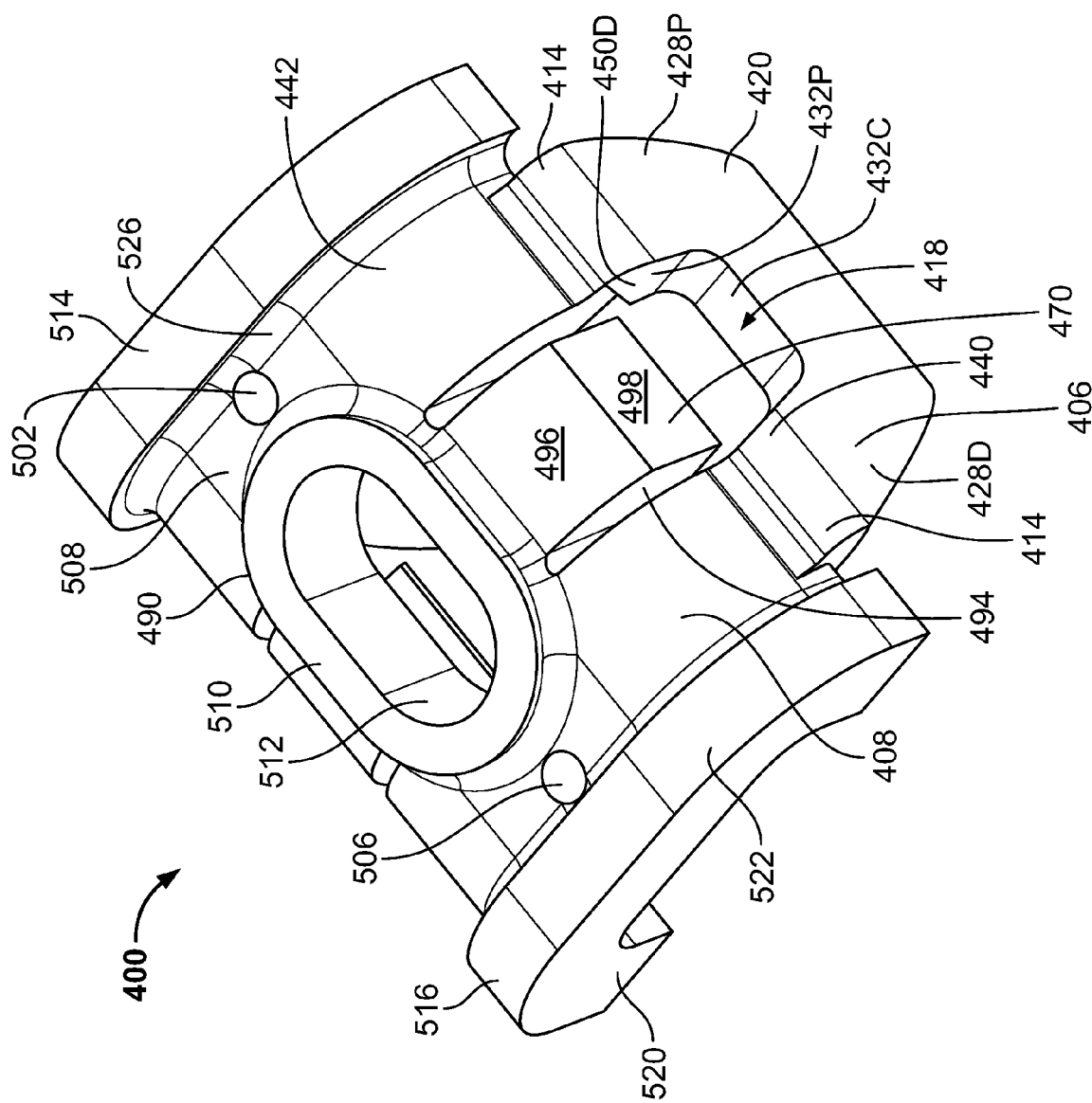
FIG. 8 is an elevated perspective view, from the front, of a second exemplary bone plate clip.
Figure 9:
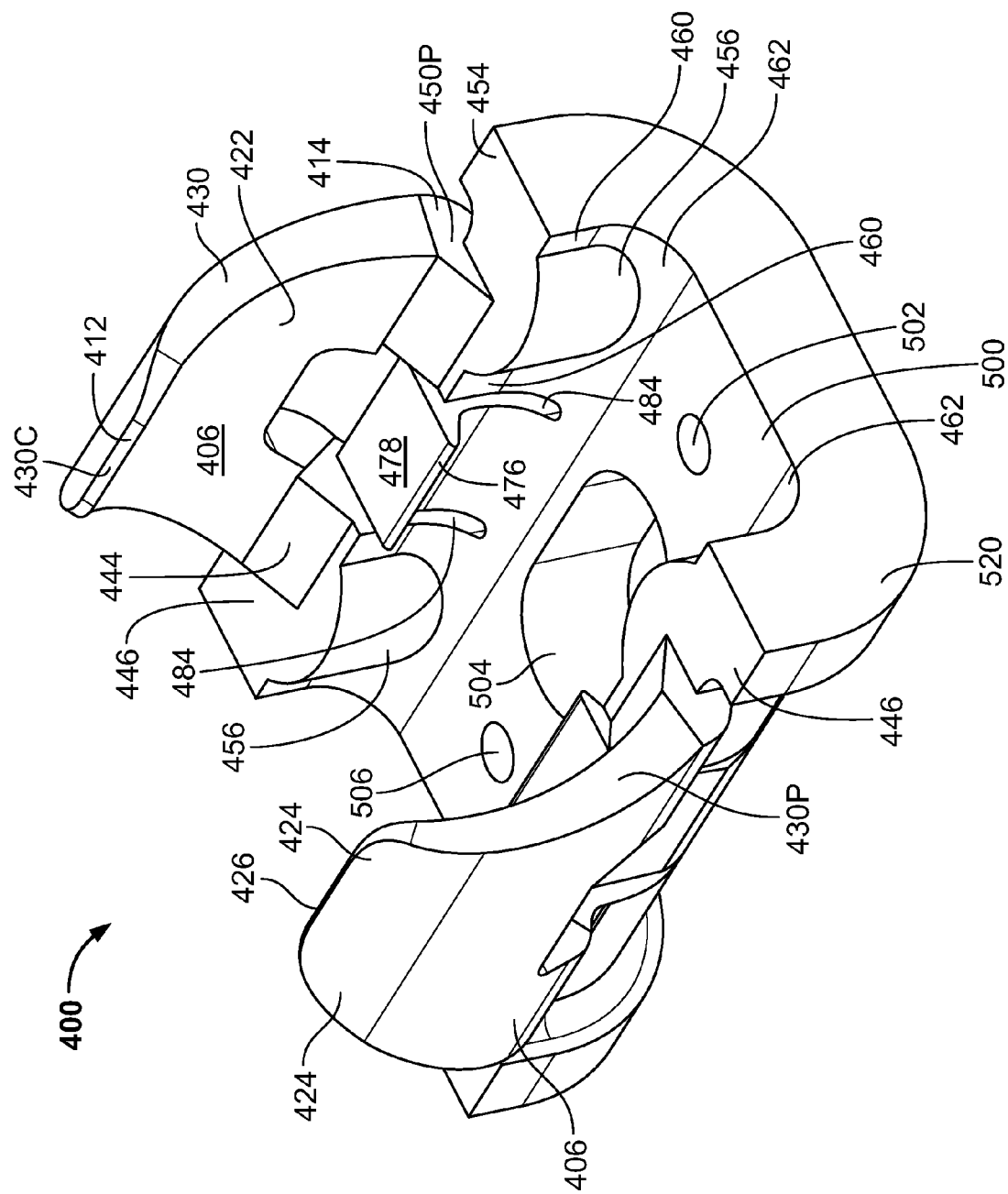
FIG. 9 is a bottom perspective view of the exemplary bone plate clip of FIG. 8.
Figure 10:
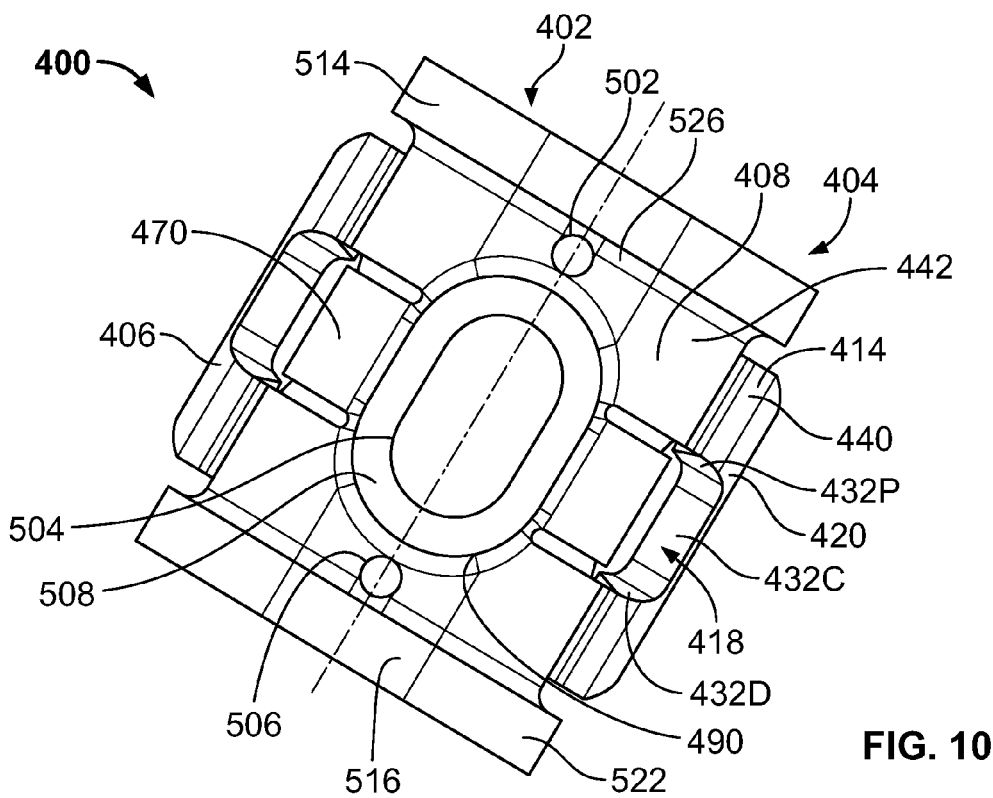
FIG. 10 is an overhead view of the exemplary bone plate clip of FIG. 8.
Figure 11:
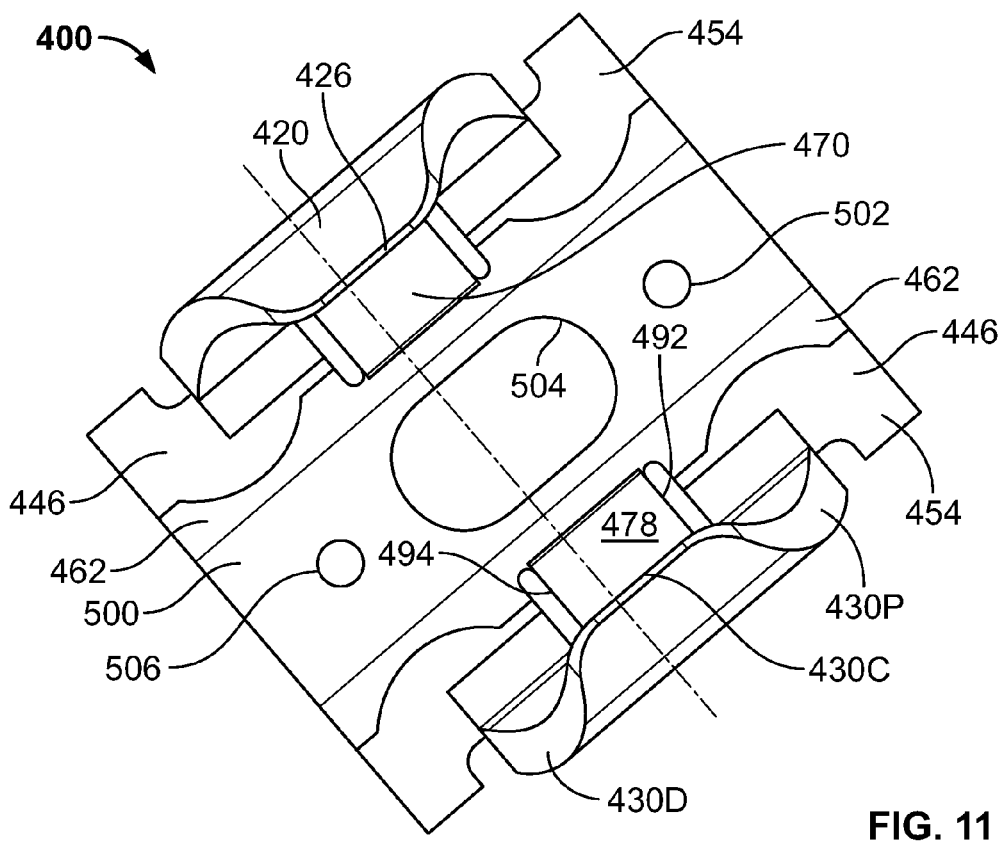
FIG. 11 is a bottom view of the exemplary bone plate clip of FIG. 8.
Figure 12:
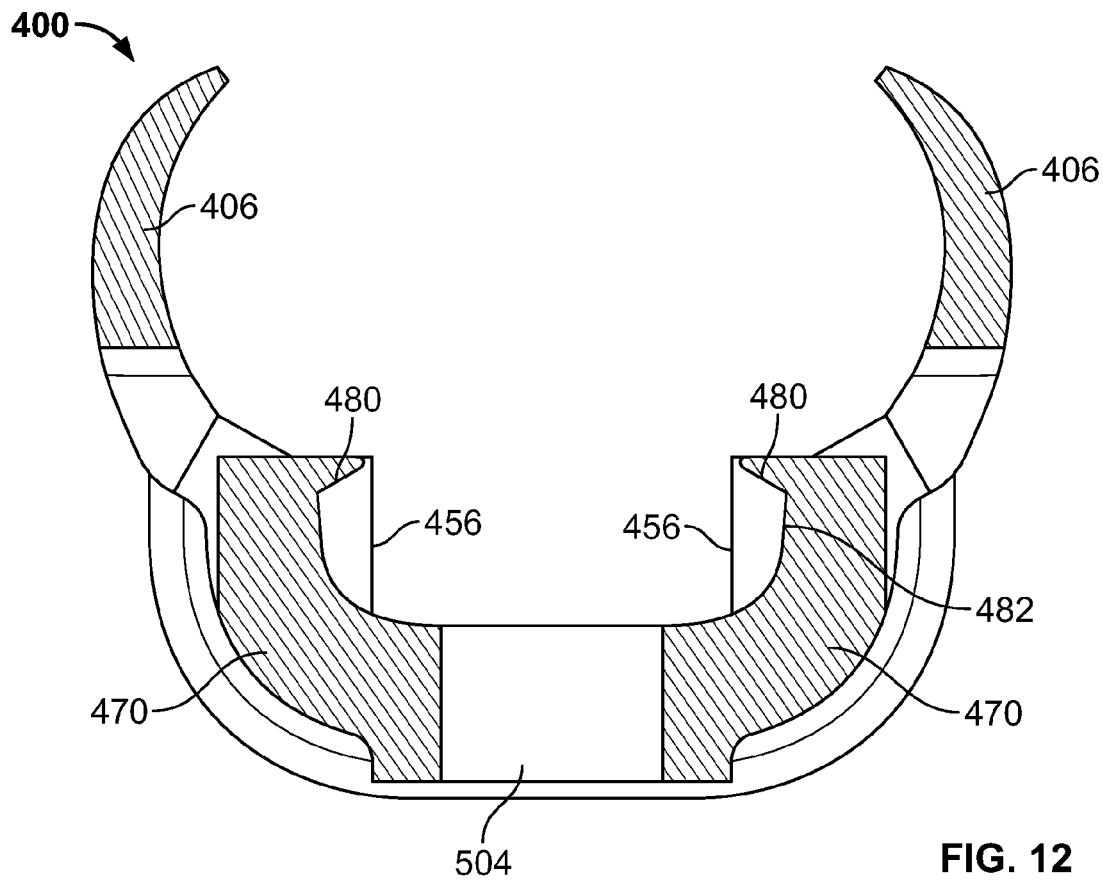
FIG. 12 is a cross-sectional view of the exemplary bone plate clip of FIG. 8.
Figure 13:
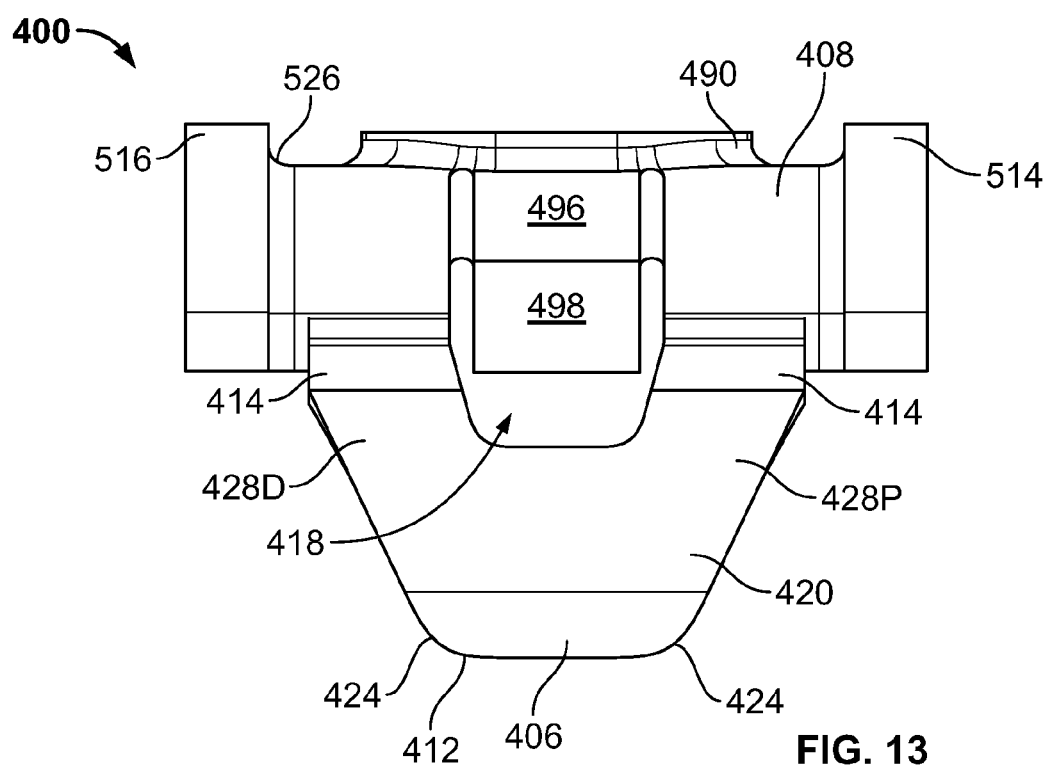
FIG. 13 is a profile view of the exemplary bone plate clip of FIG. 8.
Figure 14:
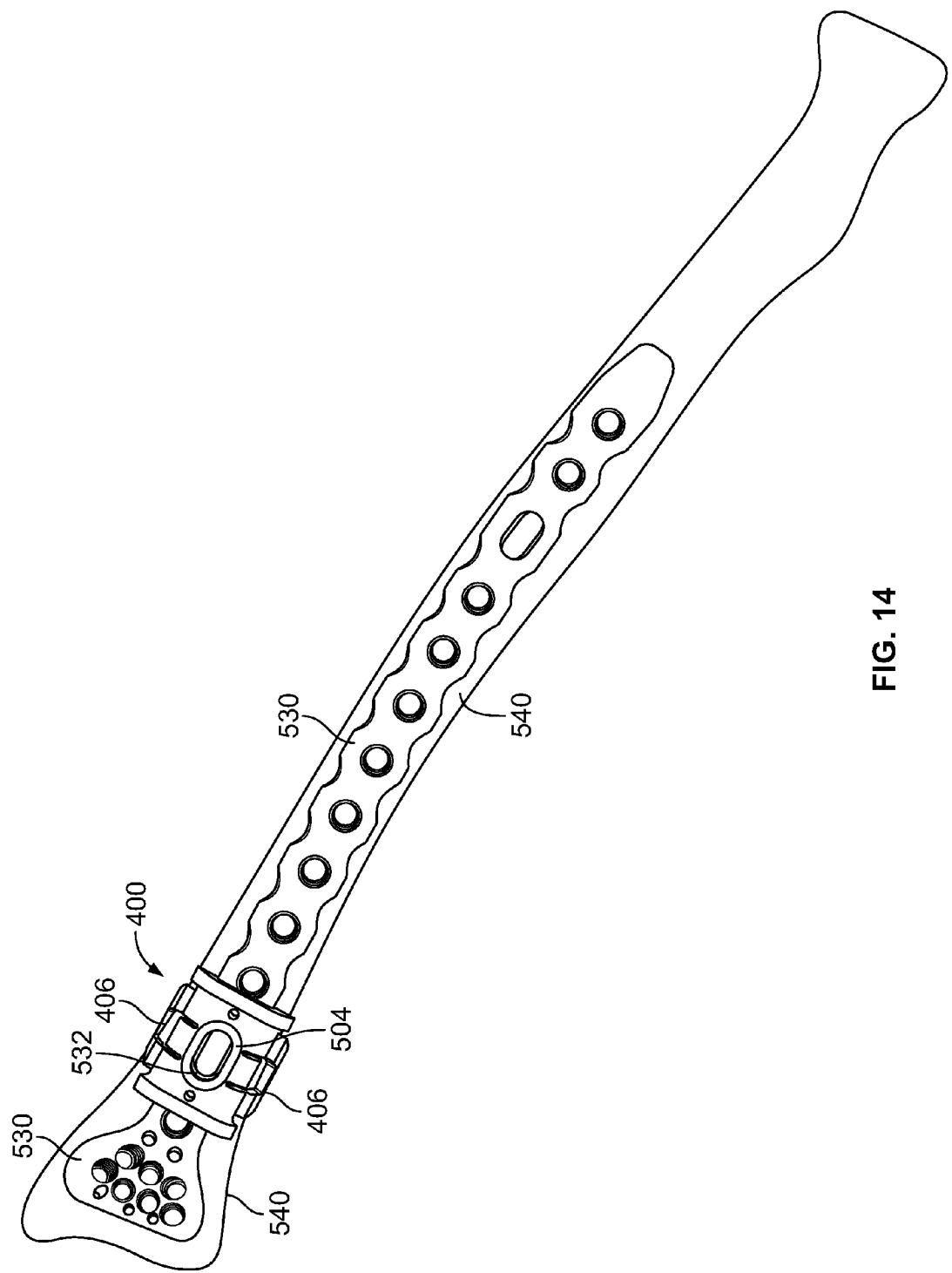
FIG. 14 is an elevated perspective view of the exemplary bone plate clip of FIG. 8 mounted to a bone plate and a bone.
Figure 15:
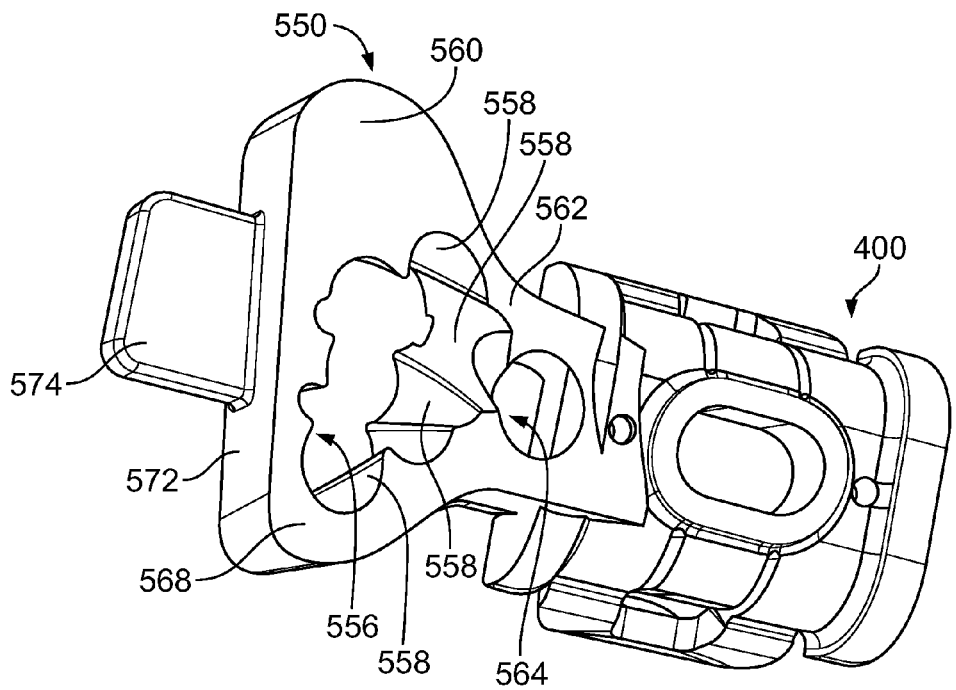
FIG. 15 is an elevated perspective view of the exemplary bone plate clip of FIG. 8 with an exemplary block.
Figure 16:
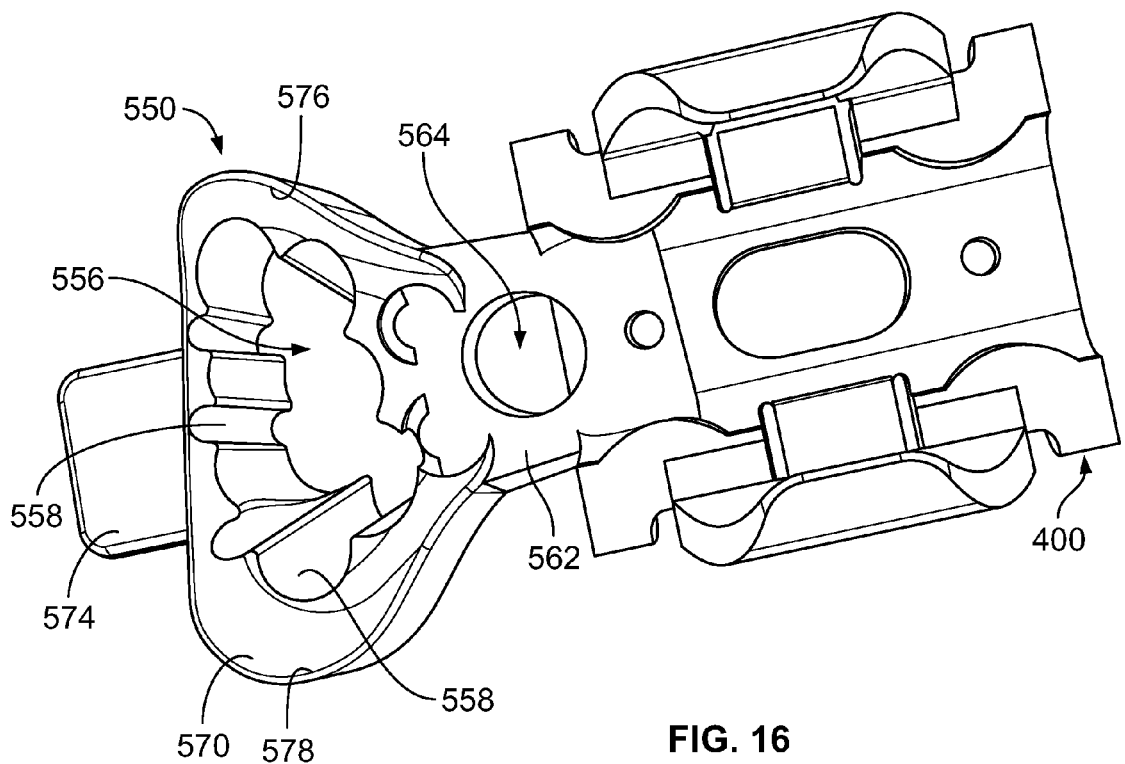
FIG. 16 is a bottom view of the exemplary bone plate clip of FIG. 8 with the exemplary block.
Figure 17:
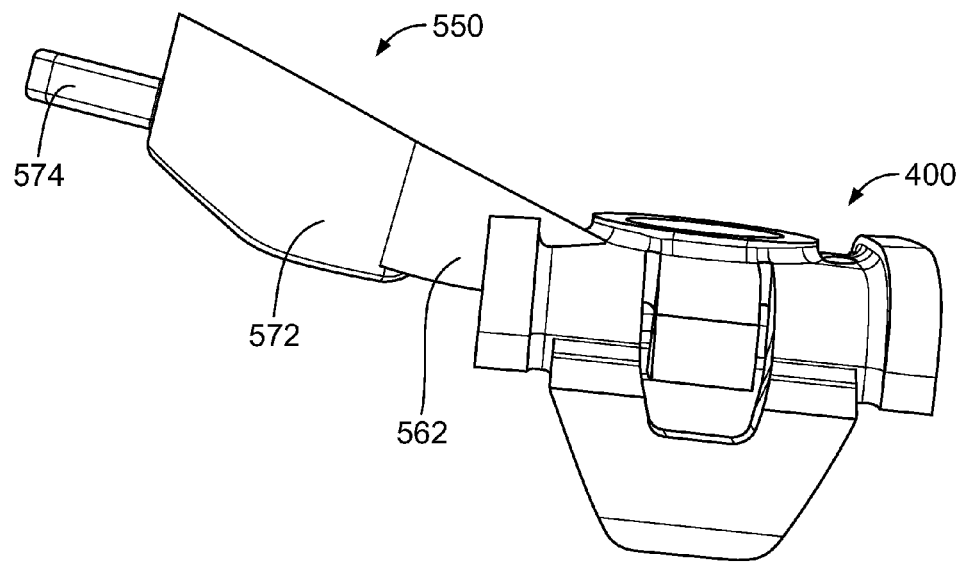
FIG. 17 is a right side profile view of the exemplary bone plate clip of FIG. 8 with the exemplary block.
Figure 18:
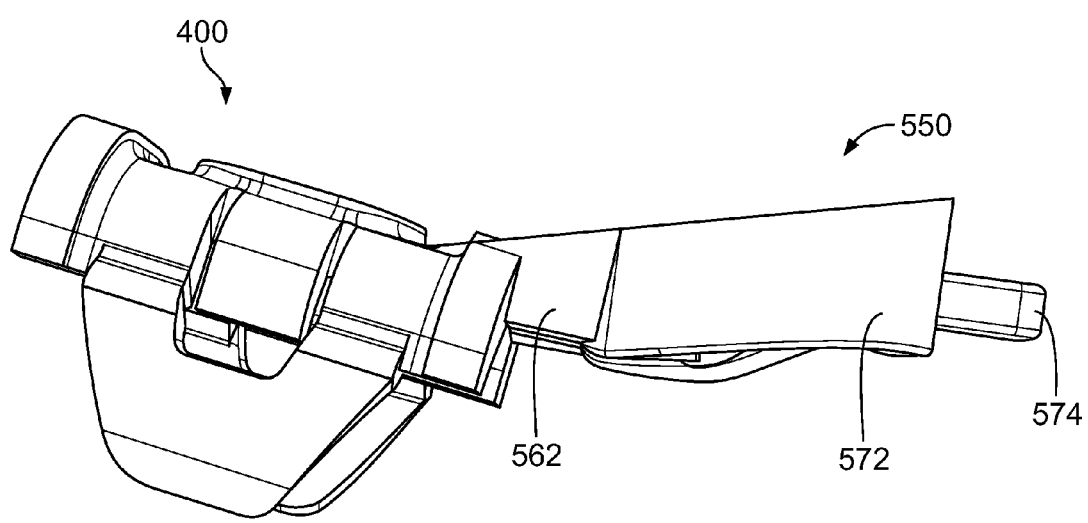
FIG. 18 is a left side profile view of the exemplary bone plate clip of FIG. 8 with the exemplary block.
Figure 19:
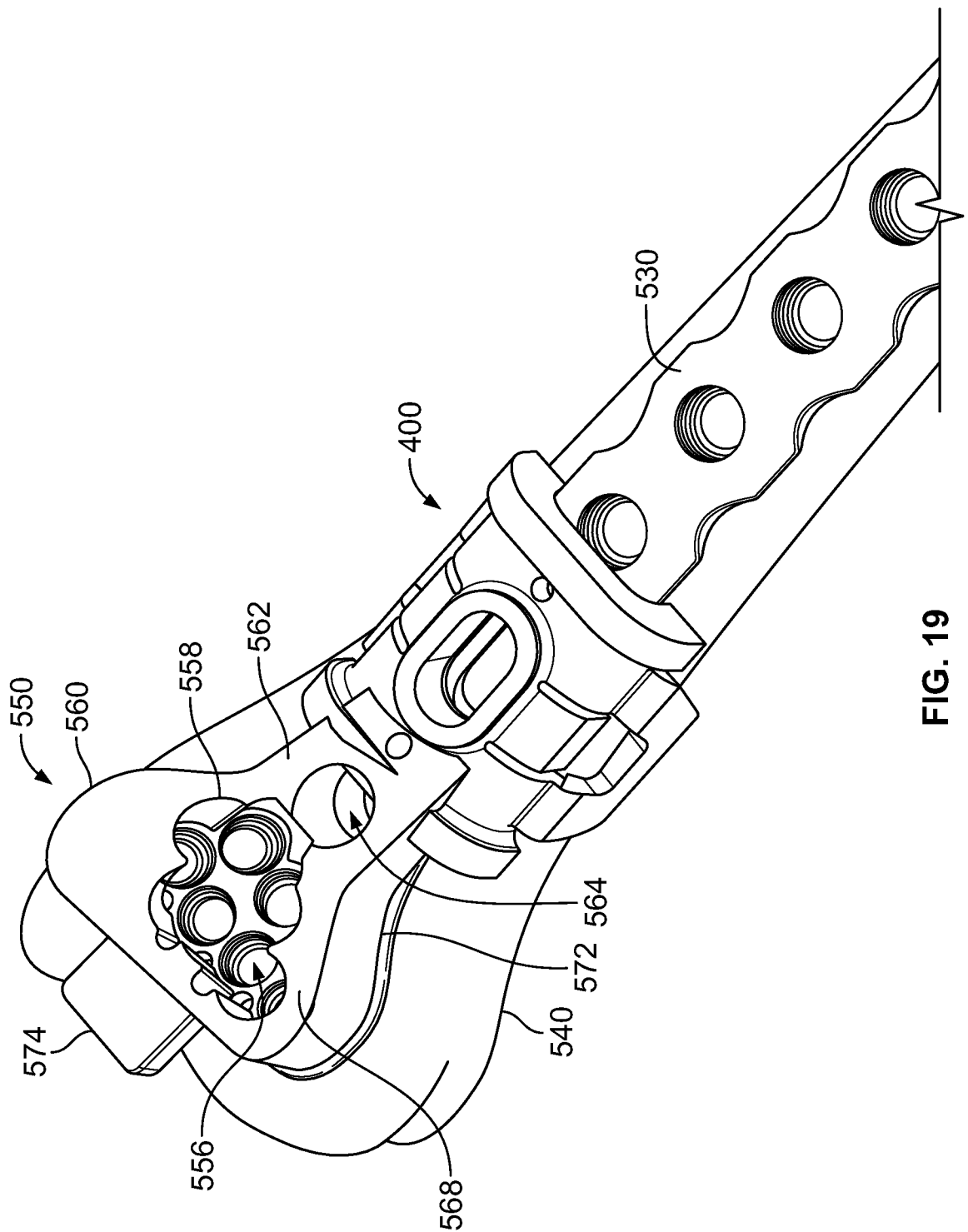
FIG. 19 is an elevated perspective view of the exemplary bone plate clip of FIG. 8 with the exemplary block being mounted to a bone and a bone plate.
Figure 20:
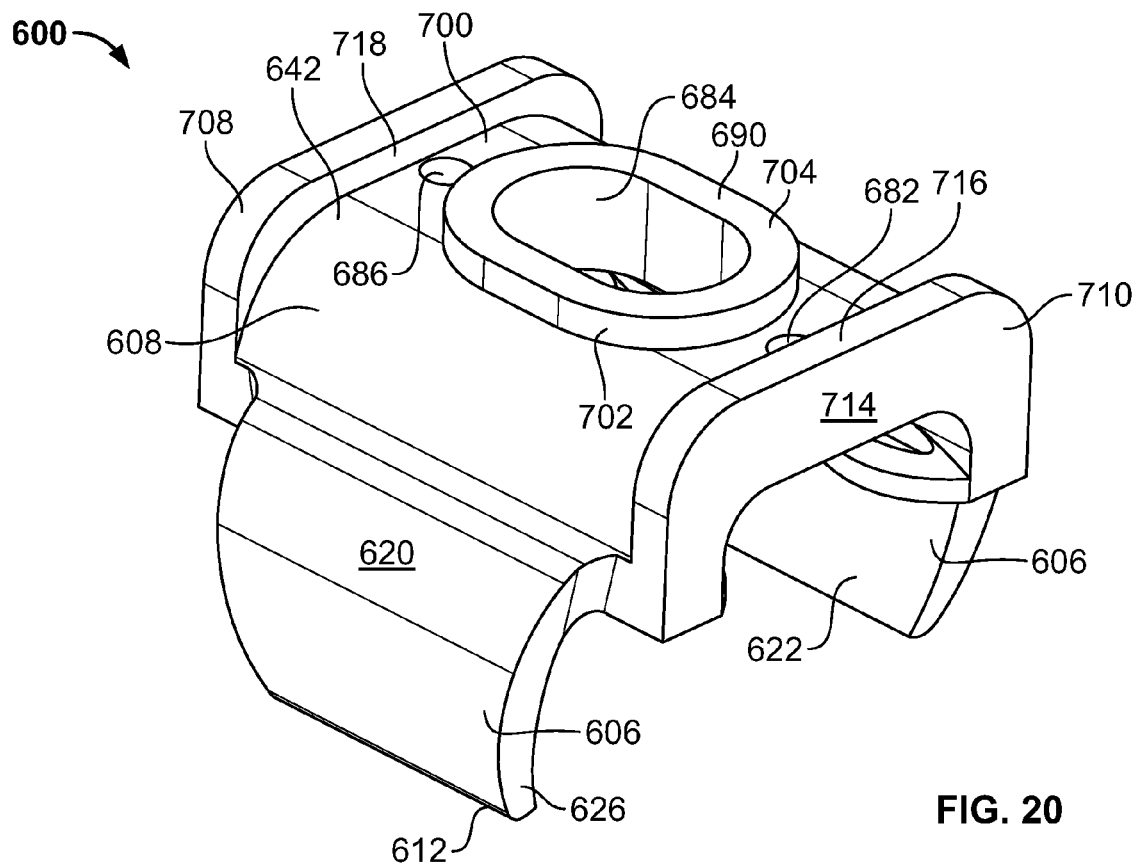
FIG. 20 is an elevated perspective view, from the front, of a second exemplary bone plate clip.
Figure 21:
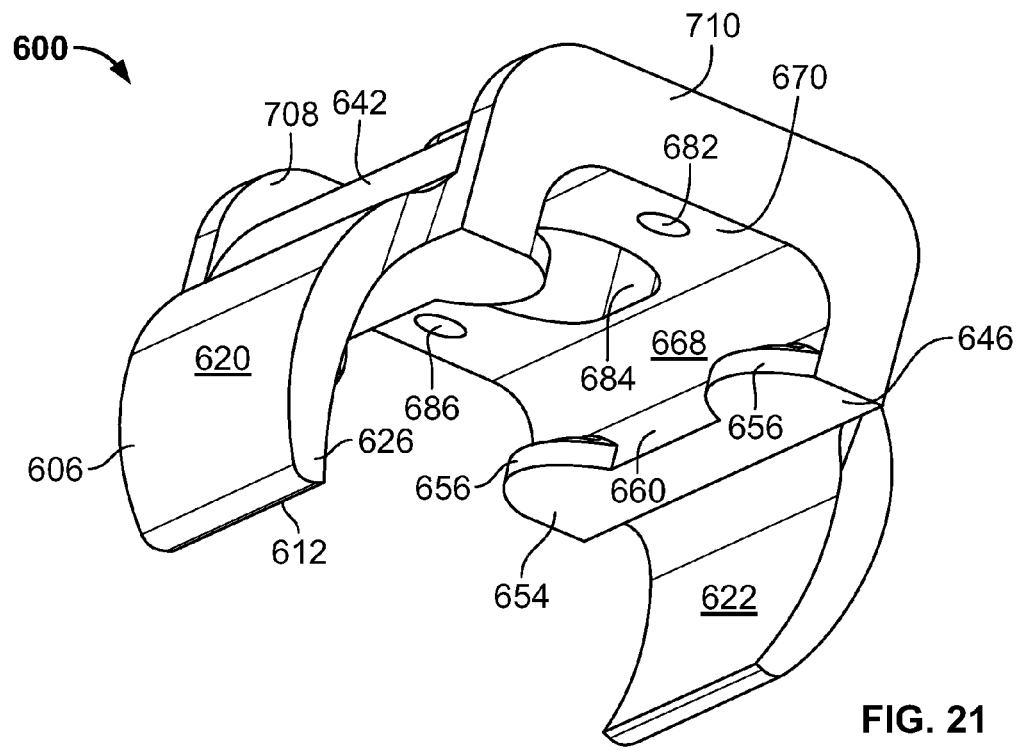
FIG. 21 is a bottom perspective view of the exemplary bone plate clip of FIG. 20.
Figure 22:
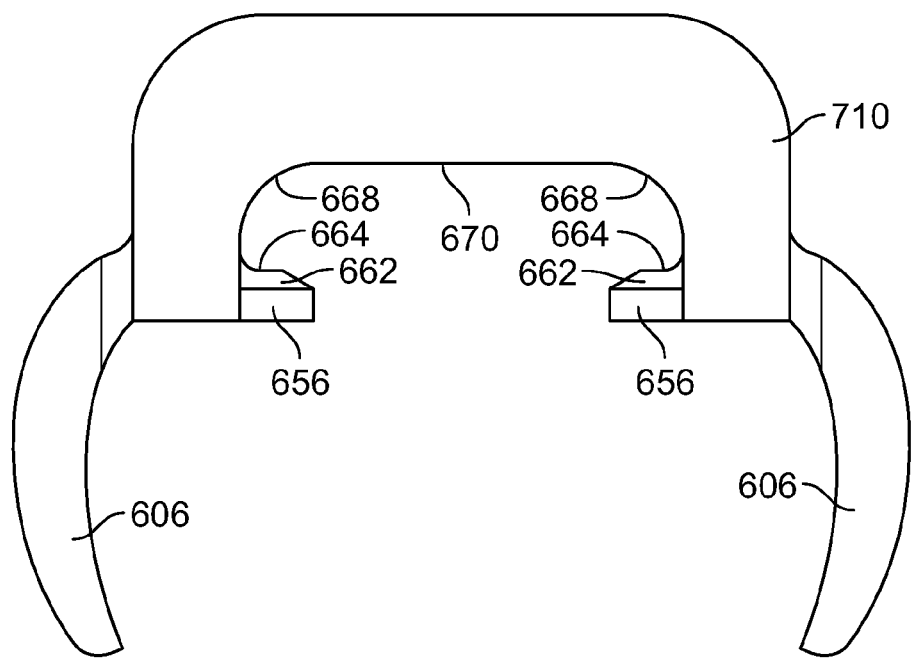
FIG. 22 is a frontal view of the exemplary bone plate clip of FIG. 20.
Figure 23:
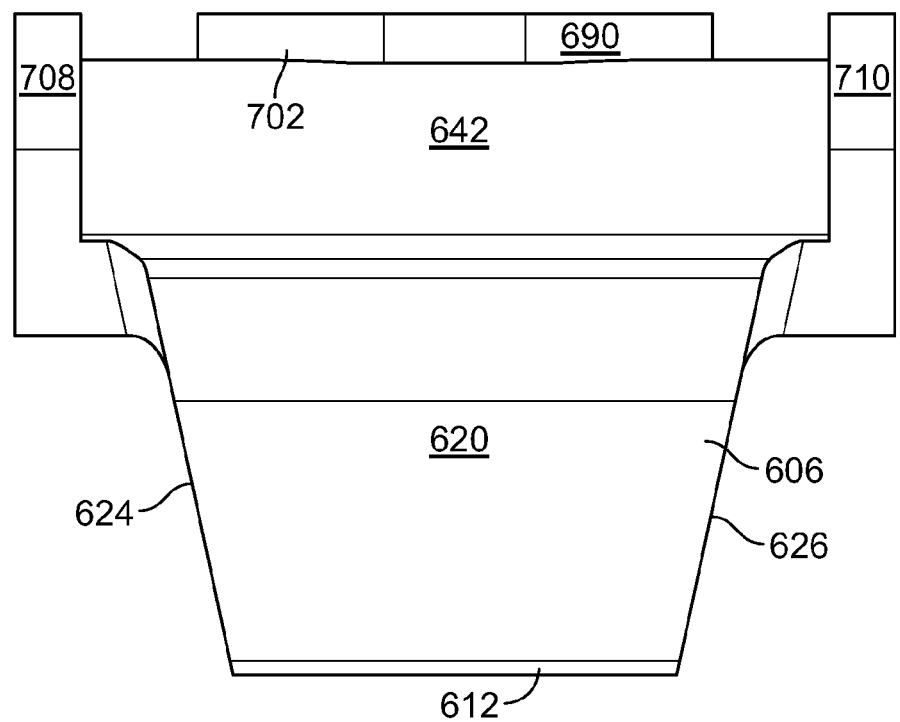
FIG. 23 is a profile view of the exemplary bone plate clip of FIG. 20.
Figure 24:
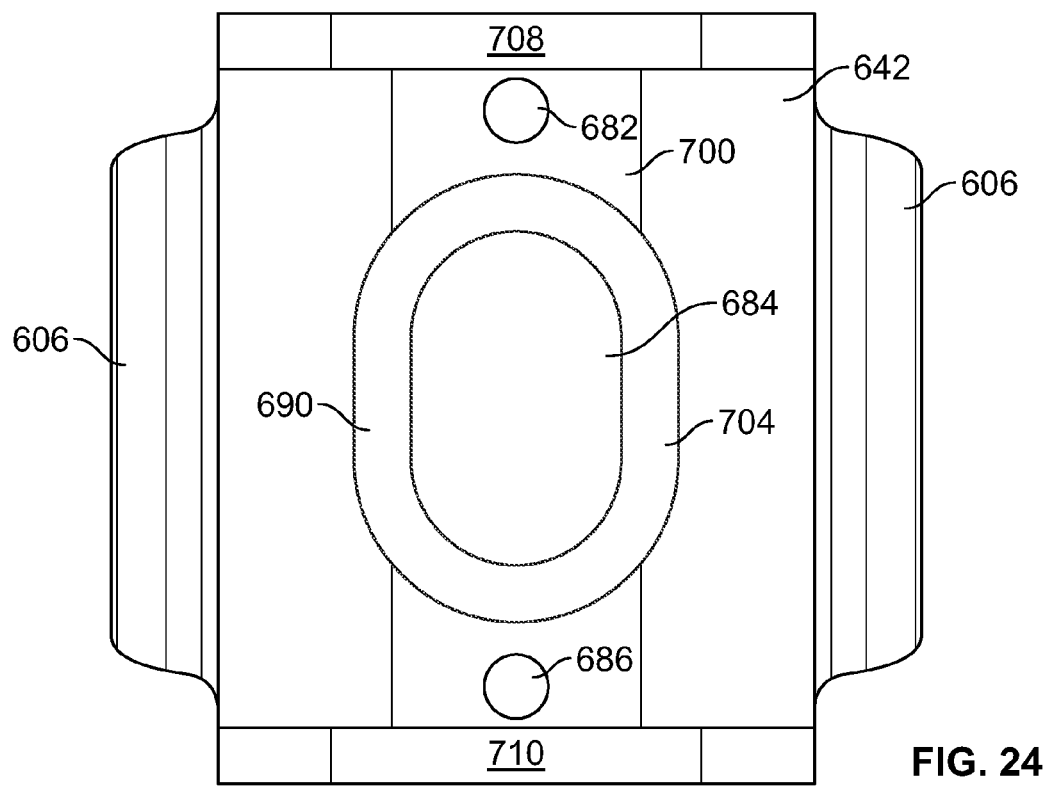
FIG. 24 is an overhead view of the exemplary bone plate clip of FIG. 20.
Figure 25:
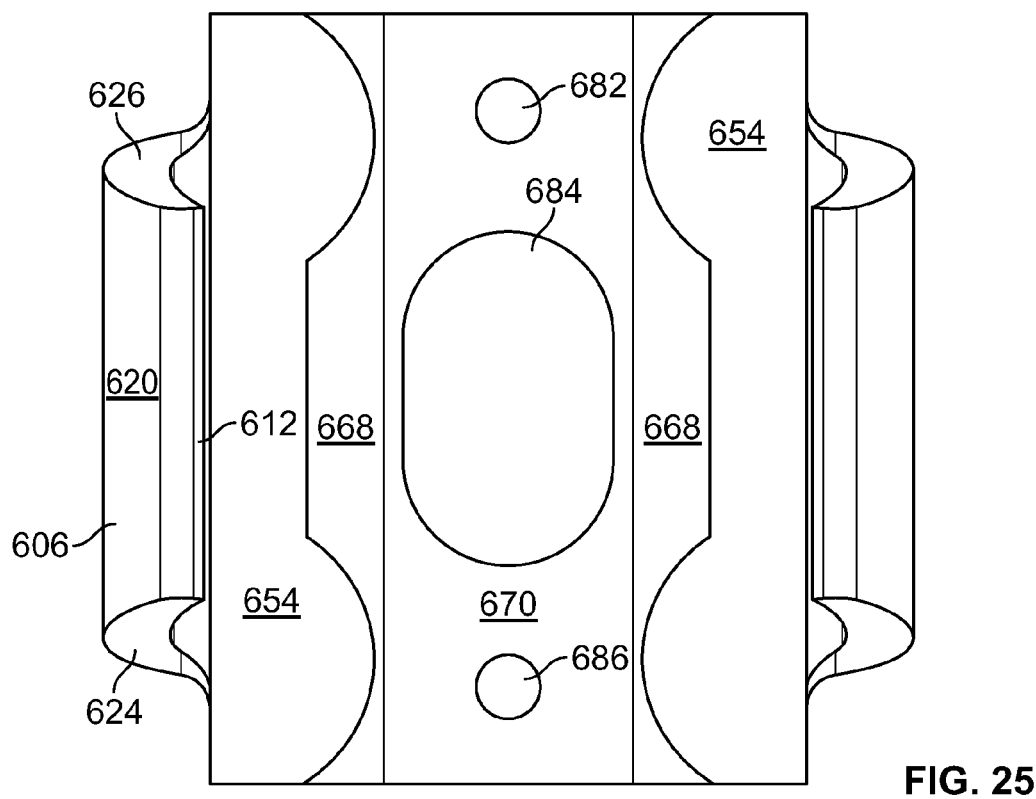
FIG. 25 is a bottom view of the exemplary bone plate clip of FIG. 20.

Referring to FIGS. 6 and 7, in order to use the scaffold 100, a surgeon clips the scaffold to the volar bone plate 304 while the volar bone plate is located outside of the patient's body. This is accomplished by aligning an elongated hole 320 of the bone plate 304 with the elongated hole 250 of the scaffold 100. Thereafter the bone plate 304 is raised to pass between the rounded ends 128, 188 of the arcuate arms 102, 104, 106, 108. In exemplary form, the medial-to-lateral spacing between the arms 102, 104, 106, 108 is wide enough so that the width of the bone plate 304 can pass therebetween. But the medial-to-lateral distance between the tabs 168, 169, 228, 229 is not great enough to allow the bone place to pass therebetween. Instead, the medial-to-lateral spacing is slightly smaller than the width of the bone plate 304. In this manner, the tabs 168, 169, 228, 229 of the scaffold 100 are temporarily deformed by pushing the bone plate 304 in between the tabs, thereby forcing the bone plate between the tabs and the bottom surface. Because the scaffold 100 is fabricated from a polymer, such as polyethylene, the tabs are somewhat elastic and return to their original position to retain the bone plate. In other words, the tabs 168, 169, 228, 229 operate to retain the bone plate 304 until the bone plate is mounted to the bone 310.

After the bone plate 304 is mounted to the scaffold 100, the bone plate and scaffold are positioned on the bone 310. Depending upon the fracture point and other factors, the surgeon tentatively positions the bone plate 304 on top of the bone 310, in this case a distal radius. Positioning of the bone plate 304 and scaffold 100 is accomplished by increasing the medial-to-lateral spacing between the rounded ends 128, 188 of the arcuate arms 102, 104, 106, 108 so that the bone is able to pass therebetween. After the bone passes beyond the rounded ends 128, 188 of the arcuate arms 102, 104, 106, 108, the elastic nature of the arms attempts to return the rounded ends to their default position, which is operative to clamp the bone 310 in between the arms. In exemplary form, the medial-to-lateral spacing of the arms is such that the arms 102, 104, 106, 108 need to be deformed to increase the medial-to-lateral spacing therebetween. But the partially elastic nature of the arms provides a spring force attempting to return the arms 102, 104, 106, 108 to their original position. This spring force is sufficient to retain the scaffold 100 in position with respect to the bone 310, which also operates to retain the general position of the bone with respect to the bone plate 304. At this time, the surgeon can drill holes through the bone plate 304 and into the bone 310 in order to more securely mount the bone plate to the bone. After one or more holes have been drilled and one or more fasteners have been secured to the bone 310 and bone plate 304, the scaffold 100 may be removed by deforming the arms 102, 104, 106, 108 in order to pass beyond the widest part of the bone, while at the same time deforming the tabs 168, 169, 228, 229 to allow the bone plate to pass therebetween and discontinue the engagement between the scaffold and bone plate.

Though not specifically discussed, it should be noted that at any time during the procedure, the surgeon may use one or more K-wires (not shown) to align the scaffold 100 with respect to the bone 310. An exemplary circumstance would be initially positioning one or more K-wires into the bone 310 and thereafter sliding the K-wire(s) through respective orifices 154, 156, 164, 166 (see FIGS. 1 and 5) of the scaffold 100 in order to align the scaffold with respect to the bone. Those skilled in the art would be familiar with such a technique in light of the embodiments disclosed herein.

Referring to FIGS. 8-13, a second exemplary clip 400 includes a generally arcuate shape to partially circumscribe a bone. The clip 400 comprises two mirror image halves 402, 404 that are seamlessly connected. For purposes of brevity, the explanations concerning the features of both halves have been consolidated as an explanation concerning one of the halves is equally applicable for the other half.

Each half includes an appendage 406 that seamlessly extends from an opposing side of a platform 408. The appendage 406 comprises a closed loop having a vertical cross-section with an arcuate profile. Each appendage 406 tapers in medial-to-lateral thickness ML along the arcuate path so that the thickness increases from a bottom edge 412 until reaching the platform 408. Likewise, each appendage 406 tapers outward in proximal-to-distal PD length until reaching a shoulder 414 just prior to reaching the platform 408. In this manner, the length of the appendage increases from the bottom edge 412 until reaching the shoulder 414, where the length remains constant until reaching the platform 408. A cutout 418 creates an opening extending through the appendage 406, through the shoulder 414, and through a portion of the platform 408.

The appendage 406 includes four exterior surfaces. A first exterior surface 420 is smooth, arcuate, and convex. This first exterior surface faces laterally outward from the remainder of the clip 400. A second exterior surface 422, is generally opposite the first exterior surface 420, and is smooth, arcuate, and concave. This second exterior surface 422 faces toward the interior of the clip 400 where the bone and bone plate are located when the clip is utilized. As discussed previously, the appendage 406 tapers in medial-to-lateral thickness ML, which results in both exterior surfaces 420, 422 having a trapezoidal appearance with a pair of rounded, corners 424 that a connected by a linear bottom edge 426. Opposite the linear edge 426, both surfaces 420, 422 include a pair of branches 428P, 428D that are interposed by the cutout 418. Each branch 428P, 428D increases in proximal-to-distal length as that portion of the branch gets closer and closer to the shoulder 414. A third exterior surface 430 is generally smooth and extends at a right angle with respect to the first and second exterior surfaces 420, 422. However, the width of the third exterior surface 430 is not constant, but rather changes indicative of the fact that the overall thickness of the appendage changes from top to bottom. More specifically, the third exterior surface 430 includes proximal and distal segments 430P, 430D that include rounded over sections transitioning to a linear, constant diameter section 430C comprising part of the bottom edge 412, which is opposite the shoulder 414. Finally, a fourth exterior surface 432 is smooth and takes on a U-shaped appearance. This U-shaped exterior surface 432 includes a pair of sections 432P, 432D that are generally opposite one another, but not in parallel. Rather the sections 432P, 432D are acutely angled with respect to one another and obtusely angled with respect to a third, intervening section 432C.

The shoulder 414 comprises two segments that are mirror images of one another. Each shoulder includes a smooth, arcuate top surface 440 that bridges a top, arcuate surface 442 of the platform 408 with the first exterior surface 420 of the appendage 406. Opposite the arcuate surface 440 is a smooth, planar surface 444 extending between the second exterior surface 422 of the appendage 406 and a bottom surface 446 of the platform 408. Interposing the arcuate surface 440 and the planar surface 444 are corresponding proximal and distal surfaces 450P, 450D. Both of these surfaces 450P, 450D extend at a right angle with respect to the arcuate surface 440, the planar surface 444, and the bottom surface 446.

The bottom surface 446 of the platform 408 is multifaceted and partially defines the boundaries of an interior of the clip 400. In particular, the bottom surface 446 of each half 402, 404 includes a raised, flat surface 454 that intersects the shoulder 414 surfaces. This raised surface 454 includes two arcuate projections that cooperate with respective arcuate walls 456 to form a pair partial cylindrical projections (two for each half 402, 404) extending into the interior of the clip 400. Each arcuate wall 456 is bordered by a vertical wall 460 and an arcuate wall 462 that partially defines a detent 470 occupying a portion of the cutout 418.

The detent 470 is integrally formed and extends from the platform 408. In exemplary form, the detent 470 includes a pointed end 476 that extends into the interior of the clip 400. Extending away from the end 476 is a flat bottom surface 478 and a flat declined surface 480. The declined surface 480 terminates in an interior surface 482 that vertically tracks the general shape of the vertical wall 460 and an arcuate wall 462. Corresponding gaps 484 occur proximally and distally on both sides of the detent 470, thereby effectively forming a peninsula mounting at one end to the platform. Because only one end of the detent 470 is mounted to any fixed structure, the detent is repositionable within the cutout 418 in the lateral and medial directions. The detent 470 also includes parallel, vertical proximal and distal walls 492, 494 that are formed at right angles to a pair of exterior surfaces 496, 498. The first exterior surface 496 generally tracks the curvature of the top, arcuate surface 442 of the platform 408, while the second exterior surface 498 is vertically oriented.

The arcuate walls 462 on the interior of the clip 400 are interposed by a generally planar horizontal surface 500 that is substantially rectangular in shape. This horizontal surface 500 includes three through holes 502, 504, 506 that extends through the platform 408. The first and third holes 502, 506 are circular in horizontal cross-section and dimensioned to each accommodate a K-wire (not shown), whereas the second hole 504 is oblong in horizontal cross-section and dimensioned to accommodate a compression screw (not shown) inserted through the top of the second hole.

At the top, arcuate surface 442 of the platform 408, a ring cap 490 partially defines the second through hole 504. The ring cap 490 is generally oblong in shape and extends vertically above the top, arcuate surface 442 and a top planar surface 508 of the platform 408. The base of the ring cap 490 tapers upward, away from the surfaces 442, 508 until reaching a horizontal ring surface 510. The horizontal ring surface 510 is oriented perpendicular to a vertical, oblong wall 512 that delineates the interior of the second through hole 504. Each of the K-wire holes 502, 506 lies generally along the centerline delineating the halves 402, 404 and respectively interposes the base of the ring cap 490 and a raised flange 514, 516 at the proximal and distal ends.

The raised flanges 514, 516 are mirror images of one another and take on a generally U-shaped profile. Each flange 514, 516 includes a planar vertical wall 520 that is perpendicular to an arched wall 522. The vertical height of the top of the arched wall 522 is slightly above the vertical height of the ring surface 510 and above the top, arcuate surface 442 of the platform 408. An arcuate wall 526 bridges between the top, arcuate surface 442 and the arched wall 522. In exemplary form, a portion of the arcuate wall 526 and a portion of the arcuate surface 442 delineate the circular top of each K-wire hole 502, 506.

In this exemplary embodiment, the clip 400 is fabricated from injection molded thermoplastic. As a result, the components and features of the clip 400 described above are integrated into a single piece structure thus giving the material some inherent elasticity and flexibility. But it should also be noted that the clip 400 need not be fabricated from a thermoplastic material or injection molded. Instead, the clip 400 may be fabricated from a metal such as, without limitation, aluminum.

Referencing FIGS. 8-14, using the exemplary clip 400 may include mounting a volar bone plate 530 while the volar bone plate is located outside of the patient's body. This is accomplished by aligning an elongated hole 532 of the bone plate 530 with the elongated hole 504 of the clip 400. Thereafter the bone plate 530 is raised to pass between the bottom edges 412 of the appendages 406. In exemplary form, the medial-to-lateral spacing between the bottom edges 412 of the appendages 406 is enough so that the width of the bone plate 530 can pass therebetween. But the default medial-to-lateral distance between the ends 476 of the detents 470 is not great enough to allow the bone place to pass therebetween. Instead, the medial-to-lateral spacing of the detent ends 476 is slightly smaller than the width of the bone plate 530. In order to elevate the bone plate 530 into the interior of the clip 400, the detents 470 are temporarily deformed by pushing the bone plate 530 in between the detents, thereby forcing the bone plate between the detents, which causes the detents to move outward away from the interior of the bone plate. Because the clip 400 is fabricated from a somewhat resilient material, such as a polymer or deformable metal, the detents 470 are somewhat elastic and return to their original position to retain the bone plate 530 after the bone plate passes into the interior and beyond the ends 476 of the detents. In this manner, the detents 470 operate to retain the bone plate 530 in a coupled engagement with the clip 400 until the bone plate is mounted to the bone 540.

After the bone plate 530 is mounted to the clip 400, the bone plate and clip are positioned on the bone 540. Depending upon the fracture point and other factors, the surgeon tentatively positions the bone plate 530 on top of the bone 540, in this case a distal radius. Positioning of the bone plate 530 and clip 400 is accomplished by increasing the medial-to-lateral spacing between the bottom edges 412 of the appendages 406 so that the bone is able to pass therebetween. After the bone passes beyond the bottom edges 412 of the appendages 406, the elastic nature of the appendages attempts to return the bottom edges to their default position, which is operative to clamp the bone 540 in between the appendages. In exemplary form, the medial-to-lateral spacing of the appendages 406 is such that the appendages need to be deformed to increase the medial-to-lateral spacing therebetween. But the partially elastic nature of the appendages 406 provides a spring force attempting to return the appendages to their original position. This spring force is sufficient to retain the clip 400 in position with respect to the bone 540, which also operates to retain the general position of the bone with respect to the bone plate 530. At this time, the surgeon can drill holes through the bone plate 530 and into the bone 540 in order to more securely mount the bone plate to the bone. After one or more holes have been drilled and one or more fasteners have been secured to the bone 540 and bone plate 530, the clip 400 may be removed by deforming the appendages 406 in order to pass beyond the widest part of the bone, while at the same time deforming the detents 470 to allow the bone plate to pass therebetween and discontinue the engagement between the clip and bone plate.

Though not specifically discussed, it should be noted that at any time during the procedure, the surgeon may use one or more K-wires (not shown) to align the clip 400 with respect to the bone 540. An exemplary circumstance would be initially positioning one or more K-wires into the bone 540 and thereafter sliding the K-wire(s) through respective orifices 502, 506 of the clip 400 in order to align the scaffold with respect to the bone. Those skilled in the art would be familiar with such a technique in light of the embodiments disclosed herein.

It should also be understood that the dimensions of the clip 400 as described herein are exemplary in nature and may be changed to accommodate various sizes and shapes of bones and bone plates. For example, the clip 400 may be enlarged for use as a femoral fracture device.

Referencing FIGS. 15-19, the second exemplary clip 400 may include a hole template 550 that may be a separate component or may be integrally formed as part of the clip. The hole template 550 operates to aid surgeons in aligning threaded drill guides (not shown) with holes extending through a bone plate 530 mounted to a bone 540. In exemplary form, the hole template 550 includes an outline that tracks the shape of a distal portion of a volar bone plate 530. More specifically, the hole template 550 includes a through orifice 556 delineated by a series of conjoined arcuate walls 558. Each of the walls 558 that partially defines the through orifice 556 is correspondingly angled so that when the drill guide (not shown) is aligned with a respective through hole of the bone plate 530, the drill guide can only be axially inserted at a single angle. In this manner, the drilled hole in the bone 540 is assured to be axially aligned with the respective through hole. Those skilled in the art are familiar with drill guides and understand the principle of the template 550 to drill holes in the bone 540 without further explanation.

The hole template 550 includes an enlarged head 560 that extends from a proximal end of the clip 400 by way of a neck 562. Extending through the neck 562 is a through hole 564 that at least partially overlaps one of the arcuate walls 558 of the through orifice 556. The enlarged head 560 tapers outward, extending distally, from the neck 562 to increase the medial and lateral dimensions of the head. In exemplary form, the head 560 includes a substantially planar top surface 568 and a cupped bottom surface 570 that is interposed by a circumferential surface 572. A distal tab 574 extends from the circumferential surface 572. Lateral and medial rims 576, 578 on the bottom surface 570 extend below the remainder of the bottom surface in order to provide medial and lateral bookends for the distal end of the volar plate.

Referring to FIGS. 20-25, a third exemplary scaffold or clip 600 includes a generally arcuate shape to partially circumscribe a bone. The clip 600 comprises two mirror image halves 602, 604 that are seamlessly connected. For purposes of brevity, the explanations concerning the features of both halves 602, 604 have been consolidated as an explanation concerning one of the halves, which is equally applicable for the other half.

Each half includes an appendage 606 that seamlessly extends from an opposing side of a platform 608. The appendage 606 includes an arcuate, vertical profile. Each appendage 606 tapers in medial-to-lateral thickness ML along the vertical, arcuate path so that the thickness increases from a bottom edge 612 until reaching the platform 608. Likewise, each appendage 606 tapers outward in proximal-to-distal PD length until reaching the platform 608.

The appendage 606 includes four exterior surfaces. A first exterior surface 620 is smooth, arcuate, and convex. This first exterior surface 620 faces laterally outward from the remainder of the clip 600 and rounds over at the bottom edge 612 to interface a second exterior surface 622. This second exterior surface is generally opposite the first exterior surface 620, and is smooth, arcuate, and concave. This second exterior surface 622 faces toward the interior of the clip 600 where the bone and bone plate are located when the clip is utilized. On the proximal and distal ends of the clip 600 are corresponding planar side surfaces 624, 626 that extend between the first and second exterior surfaces 620, 622.

A bottom surface 646 of the platform 608 is multifaceted and partially defines the boundaries of an interior of the clip 600. In particular, the bottom surface 646 of each half 602, 604 includes a raised, flat surface 654. This raised surface 654 includes two arcuate projections that cooperate with respective arcuate walls 656 to form a pair of semicircular projections (two for each half 602, 604) extending into the interior of the clip 600. Each arcuate wall 656 is partially bordered by a vertical wall 660 and a rounded wall 662 with a horizontal ledge 664. Adjacent the pair of projections and vertical wall 660 is an arcuate wall 668 that transitions into a planar roof 670. This roof 670 includes three through holes 682, 684, 686 that extends through to the platform 608. The first and third holes 682, 686 are circular in horizontal cross-section and dimensioned to each accommodate a K-wire (not shown), whereas the second hole 684 is oblong in horizontal cross-section and dimensioned to accommodate a compression screw (not shown) inserted through the top of the second hole.

A top, arcuate surface 642 of the platform 608 includes an oblong, raised ring 690 that partially defines the second through hole 684. The raised ring 690 extends vertically above the top, arcuate surface 442 and a top planar surface 700 of the platform 608. The raised ring 690 includes a vertical, circumferential surface 702 that is adjacent and angled perpendicularly to a horizontal surface 704. Each of the K-wire holes 608, 686 and the screw through hole 684 lie generally along a centerline delineating the halves 602, 604 and interpose raised flanges 708, 710 at the proximal and distal ends of the clip 600.

The raised flanges 708, 710 are mirror images of one another and take on a generally U-shaped profile. Each flange 708, 710 includes a planar vertical wall 714 that is perpendicular to an arched wall 716. The vertical height of the top of the arched wall 716 is slightly above the vertical height of the ring surface 690 and above the top, arcuate surface 642 of the platform 608. A second vertical wall 718 bridges between the top, arcuate surface 642 and the arched wall 716.

In this exemplary embodiment, the clip 600 is fabricated from injection molded thermoplastic. As a result, the components and features of the clip 600 described above are integrated into a single piece structure thus giving the material some inherent elasticity and flexibility. But it should also be noted that the clip 600 need not be fabricated from a thermoplastic material or injection molded. Instead, the clip 600 may be fabricated from a metal such as, without limitation, aluminum.

Use of the exemplary clip 600 is very similar to utilization of the first exemplary bone plate 100. In exemplary form, a surgeon clips the clip 600 to a volar bone plate (not shown) while the volar bone plate is located outside of the patient's body. This is accomplished by aligning an elongated hole of the bone plate with the elongated hole 684 of the clip 600. Thereafter the bone plate is raised to pass between the appendages 606 and into the interior of the clip 600. In exemplary form, the medial-to-lateral spacing between the appendages 606 is wide enough so that the width of the bone plate can pass therebetween. But the medial-to-lateral distance between the semicircular projections is not great enough to allow the bone place to pass therebetween. Instead, the medial-to-lateral spacing is slightly smaller than the width of the bone plate. In this manner, the semicircular projections of the clip 600 are temporarily deformed by pushing the bone plate in between the projections, thereby forcing the bone plate between the projections and the roof 670. Because the clip 600 is fabricated from a polymer, such as polyethylene, the semicircular projections are somewhat elastic and return to their original position to retain the bone plate. In other words, the semicircular projections operate to retain the bone plate until the bone plate is mounted to a bone.

After the bone plate is mounted to the clip 600, the bone plate and clip are positioned on a bone. Depending upon the fracture point and other factors, the surgeon tentatively positions the bone plate on top of the bone, in this case a distal radius for example. Positioning of the bone plate and clip 600 is accomplished by increasing the medial-to-lateral spacing between the bottom edges 612 of the appendages 606 so that the bone is able to pass therebetween. After the bone passes beyond the bottom edges 612 of the appendages 606, the elastic nature of the appendages attempts to return the appendages to their default position, which is operative to clamp the bone in between the appendages. In exemplary form, the medial-to-lateral spacing of the appendages 606 is such that the appendages need to be deformed to increase the medial-to-lateral spacing therebetween. But the partially elastic nature of the appendages 606 provides a spring force attempting to return the appendages to their original position. This spring force is sufficient to retain the clip 600 in position with respect to the bone, which also operates to retain the general position of the bone with respect to the bone plate. At this time, the surgeon can drill holes through the bone plate and into the bone in order to more securely mount the bone plate to the bone. After one or more holes have been drilled and one or more fasteners have been secured to the bone and bone plate, the clip 600 may be removed by deforming the appendages 606 in order to pass beyond the widest part of the bone, while at the same time deforming the semicircular projections to allow the bone plate to pass therebetween and discontinue the engagement between the clip and bone plate.

Though not specifically discussed, it should be noted that at any time during the procedure, the surgeon may use one or more K-wires (not shown) to align the clip 600 with respect to the bone. An exemplary circumstance would be initially positioning one or more K-wires into the bone and thereafter sliding the K-wire(s) through respective orifices 682, 686 (see FIGS. 20 and 21) of the clip 600 in order to align the clip with respect to the bone. Those skilled in the art would be familiar with such a technique in light of the embodiments disclosed herein.

It should also be understood that the dimensions of the clip and scaffold as described herein are exemplary in nature and may be changed to accommodate various sizes and shapes of bones and bone plates. For example, the clip and scaffold may be enlarged for use as a femoral fracture device. As used herein, the term scaffold is synonymous with clip and vice versa.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly, stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A device to maintain temporary engagement with a bone plate and a bone, the device comprising:
   a first biased appendage positioned opposite a second biased appendage, the first and second biased appendages including an arcuate vertical profile that partially defines an interior region that is adapted to partially surround the bone;
   a platform concurrently coupled to the first and second biased appendages, the platform also partially defining the interior region, the platform including a through hole open to the interior region from a top surface of the platform; and,
   a first tab extending into the interior region from at least one of the first biased appendage, the second biased appendage, and the platform, the first tab having a first inclined surface that is adapted to engage a bone plate and a second surface that is substantially parallel to the top surface of the platform and adapted to engage a portion of the bone as the bone is partially surrounded by the first and second biased appendages.

2. The device of claim 1, further comprising a third biased appendage positioned opposite a fourth biased appendage, the third and fourth biased appendages including an arcuate vertical profile that partially defines the interior region, wherein the first and third biased appendages are spaced apart in a proximal-to-distal direction, and wherein the first and second biased appendages are spaced apart in a medial-to-lateral direction perpendicular to the proximal-to-distal direction.

3. The device of claim 1, wherein at least one of the first and second biased appendages and the platform includes a K-wire hole.

4. The device of claim 3, wherein at least one of the first and second biased appendages and the platform include a plurality of K-wire holes.

5. The device of claim 1, wherein:
the platform includes an arcuate medial-to-lateral profile; and,
the first and second biased appendages seamlessly extend from the platform.

6. The device of claim 1, wherein:
the platform includes at least one K-wire hole extending into the interior region; and,
the through hole of the platform comprises an oblong through hole sized to receive a threaded fastener.

7. The device of claim 1, wherein:
the first tab extends from a bottom surface of the platform;
the bottom surface of the platform includes a second tab spaced apart from the first tab in a medial-to-lateral direction;
the first biased appendage is spaced apart from the second biased appendage in the medial-to-lateral direction; and,
the first and second tabs cooperate to decrease a widthwise gap in the interior region extending in the medial-to-lateral direction.

8. The device of claim 1, further comprising a second tab extending from at least one of the first biased appendage, the second biased appendage, and the platform, the second tab extending into the interior region and adapted to engage the bone plate, wherein:
the second tab is spaced apart from the first tap in the medial-to-lateral direction;
the first and second tabs cooperate to decrease a first widthwise gap in the interior region extending in the medial-to-lateral direction.

9. The device of claim 2, further comprising:
a second tab extending from at least one of the first biased appendage, the second biased appendage, and the platform, the second tab extending into the interior region and adapted to engage the bone plate;
a third tab extending from at least one of the first biased appendage, the second biased appendage, and the platform, the third tab extending into the interior region and adapted to engage the bone plate;
a fourth tab extending from at least one of the first biased appendage, the second biased appendage, and the platform, the fourth tab extending into the interior region and adapted to engage a bone plate;
wherein the second tab is spaced apart from the first tab in the medial-to-lateral direction and cooperate to decrease a first widthwise gap in the interior region extending in the medial-to-lateral direction;
wherein the fourth tab is spaced apart from the third tab in the medial-to-lateral direction and cooperate to decrease a second widthwise gap in the interior region extending in the medial-to-lateral direction; and,
wherein the first tab is spaced apart from the third tab in the proximal-to-distal direction.

10. The device of claim 9, wherein:
the first tab extends from the first biased appendage;
the second tab extends from the second biased appendage;
the third tab extends from the third biased appendage; and,
the fourth tab extends from the fourth biased appendage.

11. The device of claim 1, further comprising a drill guide block operatively coupled to at least one of the first biased appendage, the second biased appendage, and the platform, the drill guide block including at least one through orifice.

12. The device of claim 11, wherein the drill guide block includes a through orifice partially defined by a plurality of arcuate walls.

13. The device of claim 11, wherein the drill guide block is integrally formed with at least one of the first biased appendage, the second biased appendage, and the platform.

14. The device of claim 13, wherein:
the first biased appendage, the second biased appendage, and the platform are integrally formed; and,
the drill guide block is integrally formed with the first biased appendage, the second biased appendage, and the platform.

15. The device of claim 11, wherein the drill guide block is shaped to conform to a volar bone plate.

16. The device of claim 1, wherein:
the through hole of the platform comprises an oblong through hole adapted to receive a threaded fastener; and,
at least a portion of the oblong through hole is delineated by an oblong ring upstanding from the top surface of the platform.

17. The device of claim 1, wherein:
the arcuate profile of the first biased appendage creates a concave side and an opposite convex side;
the arcuate profile of the second biased appendage creates a concave side and an opposite convex side; and,
the concave side of the first biased appendage faces the concave side of the second biased appendage.

18. The device of claim 2, wherein:
the arcuate profile of the first biased appendage creates a concave side and an opposite convex side;
the arcuate profile of the second biased appendage creates a concave side and an opposite convex side;
the arcuate profile of the third biased appendage creates a concave side and an opposite convex side;
the arcuate profile of the fourth biased appendage creates a concave side and an opposite convex side;
the concave side of the first biased appendage faces the concave side of the second biased appendage; and,
the concave side of the third biased appendage faces the concave side of the fourth biased appendage.

19. A device to maintain temporary engagement with a bone plate and a bone, the device comprising:
a first biased appendage having a vertical arcuate profile that bows outward in a medial direction;
a second biased appendage positioned opposite the first biased appendage, the second biased appendage having a vertical arcuate profile that bows outward in a lateral direction, opposite the medial direction;
a platform concurrently coupled to the first and second biased appendages, the platform cooperating with the first biased appendage and the second biased appendage to partially define an interior region that is adapted to partially surround the bone, the platform including an oblong through hole open to the interior region from a top surface of the platform; and a first tab extending into the interior region from at least one of the first biased appendage, the second biased appendage, and the platform, the first tab having a first inclined surface that is adapted to engage a bone plate and a second surface that is substantially parallel to the top surface of the platform and adapted to engage a portion of the bone as the bone is partially surrounded by the first and second biased appendages;

wherein at least one of the first biased appendage, the second biased appendage, and the platform includes a K-wire hole extending therethrough.

* * * * *